United States Patent
Li et al.

(10) Patent No.: US 7,326,710 B2
(45) Date of Patent: Feb. 5, 2008

(54) ARALKYL FORMYL-ALKYL PIPERAZINE DERIVATIVES AND THEIR USES AS A CEREBRAL NERVE PROTECTIVE AGENT

(75) Inventors: Jianqi Li, Shanghai (CN); Liying Huang, Shanghai (CN); Yang Min, Shanghai (CN); Zhijie Weng, Shanghai (CN); Chunnian Zhang, Shanghai (CN)

(73) Assignee: Shanghai Institute of Pharmaceutical Industry, Shanghai (CN)

( * ) Notice: Subject to any disclaimer, the term of this patent is extended or adjusted under 35 U.S.C. 154(b) by 465 days.

(21) Appl. No.: 10/513,699

(22) PCT Filed: Apr. 16, 2003

(86) PCT No.: PCT/CN03/00273

§ 371 (c)(1),
(2), (4) Date: Nov. 8, 2004

(87) PCT Pub. No.: WO03/095437

PCT Pub. Date: Nov. 20, 2003

(65) Prior Publication Data

US 2005/0153981 A1    Jul. 14, 2005

(30) Foreign Application Priority Data

May 8, 2002    (CN) .................. 02 1 11614

(51) Int. Cl.
*A61K 31/497* (2006.01)
*A61K 31/4965* (2006.01)
*C07D 241/04* (2006.01)
*C07D 295/00* (2006.01)
*C07D 401/00* (2006.01)
*C07D 405/00* (2006.01)

(52) U.S. Cl. ............ 514/252.13; 514/255.01; 514/255.05; 544/358; 544/360; 544/363; 544/377

(58) Field of Classification Search ............ None
See application file for complete search history.

(56) References Cited

U.S. PATENT DOCUMENTS 4,806,536 A    2/1989   Cross et al.

FOREIGN PATENT DOCUMENTS

| CN | 87100652 A | 8/1987 |
|----|------------|--------|
| CN | 1128026 A | 7/1996 |
| CN | 1293669 A | 5/2001 |
| WO | WO 97/06802 A | 2/1997 |

OTHER PUBLICATIONS

Ting et al., Synthesis and NK1/NK2 Receptor Activity of Substituted-4(Z)-(methoxyimino)pentyl-1-piperazines, Bioorganic & Medicinal Chemistry Letters, vol. 10, pp. 2333-2335 (2000).*
Takanashi, Y., et al., Neuroprotection by Intrathecal Application of Liposome-entrapped Fasudil in a Rat Model of Ischemia, Neurol. Med. Chir. (Tokyo) 41, 107-114, 2001.*
Feuerstein et al., Animal models of stroke, Molecular Medicine Today, 2000, 6: 133-135.
Isozumi et al., Experimental models and treatment trials for cerebral infarction, Tokai J Exp Clin Med, 1998, 23(3): 103-17).

* cited by examiner

*Primary Examiner*—James O. Wilson
*Assistant Examiner*—Erich Leeser
(74) *Attorney, Agent, or Firm*—Crowell & Moring LLP

(57) ABSTRACT

Aralkyl formyl alkyl piperazine derivatives

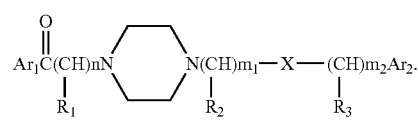

Pharmaceutical compositions comprising the same, and methods of using them as a neuroprotective agent. Pharmaceutical results indicate that these compounds have excellent neuroprotective activities and fewer side effects.

14 Claims, 1 Drawing Sheet

ARALKYL FORMYL-ALKYL PIPERAZINE DERIVATIVES AND THEIR USES AS A CEREBRAL NERVE PROTECTIVE AGENT

FIELD OF INVENTION

This invention relates to aralkyl formylalkyl piperazine derivatives and their applications as a neuro-protective agent.

TECHNICAL BACKGROUND

Cerebral accidents (such as stroke), especially ischemic apoplexy, is currently the third biggest cause of death. It is also the major factor that causes long-term loss of living abilities. In developed countries, strokes make up 10% of the death among men and 17% of the death among women. With the aging of population, it is predicted that there will be a rise of 13% in stroke patients during the next 3 years. Three fourths of stroke survivors will be disabled or dysfunctional, which results in highly increased medical cost and other serious social problems.

There are now two kinds of therapeutic medicines for the treatment of ischemic apoplexy:

1. Drugs, which induce the ischemia areas to reperfusion, and open up blocked blood vessels, resulting in recovery of cerebral blood flow, and survival of ischemic brain tissue. These agents are mainly thrombolytics, anticoagulants, vasodilators, radical cleansers, brain function accelerants and thrombolytic compositions of Chinese medicines.

2. Neuroprotective agents, which prevent damage to nerves caused by ischemia during the early stage of acute ischemic apoplexy.

The safety and efficiency of the first category of medicines are controversial, especially because of individual differences of patients. In particular, some of the drugs may cause unwanted bleeding aggravating ischemia and its symptoms and increasing the early stage mortality rate. Therefore, their clinical use has been limited.

The second category of medicines is neuroprotecting agents. Studies show that when the brain is in an ischemic state, Excitatory Amino Acid (EAA), a central neurotransmitter, is released in large amounts, acts on EAA receptors, mostly on the effector-comlex (N-methyl-D-aspartate receptor, NMDA receptor), and then opens the $Ca^{2+}$ and $Na^{2+}$ channels, changes the ion permeability, and causes imbalance of the ions inside and outside of the neural cells. This primarily will result in large in-flow the $Ca^{2+}$ and $Na^{2+}$, which causes swelling and death of nerve cells. In theory, if the activity of NMDA receptor is inhibited partly, the in-flow of $Ca^{2+}$ can be reduced greatly, and then the ischemic brain injury induced by NMDA receptor will be effectively prevented.

Recent discoveries of different kinds of EAA receptor antagonists have enabled a new approach to treating ischemic brain injuries. Among them, NMDA receptor antagonists are the main candidates for developing new drugs for preventing and treating ischemic apoplexy. Many NMDA receptor antagonists such as GV-150526A, AR-R15896, ACEA-1021, and ZD-9379 are being tested in clinical phases.

NMDA receptor competitive antagonists have two acid groups and high polarity, and are hard to permeate the blood-brain barrier. Their oral bioavailability is low. The piperazine derivative CPP and its analogues are highly selective, strong receptor antagonists, can permeate the blood-brain barrier and have activity after oral administration (Fritz, K. I., Brain Res. 729(1) 66-74, 1996). Ly-274614 is now one of the most effective NMDA receptor competitive antagonists (Cheung, N. S., Eur. J. Pharmacol., 313(1/2), 159-162, 1996). However, the above-mentioned antagonists have low therapeutic index, with side effects such as damages to motor neuron.

Disjunctive anesthetics acting on cation channel such as PCP and MK-801 are all non-competitive antagonists. These non-competitive antagonists can easily permeate the blood brain barrier; however, they have low selectivity and serious toxicity. Thus they have no or little clinical value.

Since the 1990s, new compounds have been continuously entering clinical trials. It is a long and hard task in this research area to design and synthesize selective and effective NMDA receptor modulators, and the novel antagonists with the lowest psychic and mental toxicities. This task also has great social and economic values.

DESCRIPTION OF THE INVENTION

The first aspect of the present invention is to provide aralkyl formylalkyl piperazine derivatives which have medical value. The aim is to overcome the defects of some present anti-ischemic apoplexy agents, such as induced bleeding, difficulty on transmitting blood brain barrier, low oral bioavailability, low selectivity and high nervous and behavioral toxicities.

The second aspect of the present invention is to provide the application of the above aralkyl formylalkyl piperazine derivatives as neuroprotective agents, especially in the treatment of ischemic cerebral apoplexy.

The third aspect of the present invention is to supply pharmaceutical compositions for the treatment of ischemic cerebral apoplexy.

The aralkyl formylalkyl piperazine derivatives described in present invention are free base or salts of the compounds represented by the following general formula:

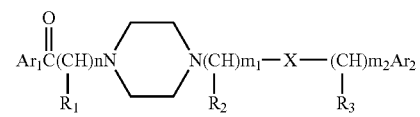

in which the salts are independently one of hydrochloride, hydrobromide, sulfate, trifluoroacetate or methanesulfonate, and preferably hydrochloride or hydrobromide. The salt can contain between 0.5-3 molecules of hydrate water.

In the above formula, $Ar_1$ and $Ar_2$ independently represent:

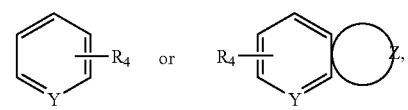

each of $R_1$, $R_2$, $R_3$ and $R_4$ can represent any one of hydrogen, a $C_1$-$C_3$ alkyl group, a $C_5$ or $C_6$ cycloalkyl group, phenyl, substituted phenyl, hydroxyl, methoxy, ethoxy, amino, substituted amino, halogen, carboxylic acid, carboxylic ester, nitryl or acetonitrile grouping;

$R_1$, $R_2$ and $R_3$ represent preferably any one of hydrogen, an alkyl group having $C_1$-$C_3$, hydroxyl, amino, substituted amino, carboxylic ester; $R_4$ is preferably hydrogen, hydroxyl, alkoxy, nitryl, halogen, amino, substituted amino or a $C_1$-$C_3$ alkyl group;

X represents one of —CHOH—, —CO—, —CONH—, —CH=CH—, O, N, —SO$_2$— or —SO—;

X is preferably one of —CHOH—, —CO— or —CONH—;

Y represents one of C, N, or O.

Y is preferably C or N.

Z represents a five or six-member ring containing at least one of C, S, N or O; and n, $m_1$ and $m_2$ are independently 0, 1, 2, or 3.

The preferable compounds are included as follows:

| Code | Chemical Name |
|---|---|
| IV-1 | $N^1$-benzoyl-$N^4$-phenacyl-piperazine, |
| IV-2 | $N^1$,$N^4$-diphenacyl-piperazine, |
| IV-3 | $N^1$-(4-nitrobenzoyl)-$N^4$-phenacyl-piperazine, |
| IV-4 | $N^1$-(2-acetoxy-1-oxo-2-phenylethyl)-$N^4$-(1-benzoylethyl) piperazine, |
| IV-5 | $N^1$-phenacyl-$N^4$-(4-chlorophenacyl) piperazine, |
| IV-6 | $N^1$,$N^4$-di (4-chlorophenacyl) piperazine, |
| IV-7 | $N^1$-(2-naphthoylmethyl)-$N^4$-phenacyl-piperazine, |
| IV-8 | $N^1$-(1-benzoylethyl)-$N^4$-phenacyl-piperazine, |
| IV-9 | $N^1$-phenacyl-$N^4$-(4-methoxyphenacyl) piperazine, |
| IV-10 | $N^1$,$N^4$-di (1-benzoylethyl) piperazine, |
| IV-11 | $N^1$-phenacyl-$N^4$-(4-nitrophenacyl) piperazine, |
| IV-12 | $N^1$-phenylacetyl-$N^4$-phenacyl-piperazine, |
| IV-13 | $N^1$-(1-benzoylethyl)-$N^4$-phenacyl-piperazine, |
| IV-14 | $N^1$,$N^4$-di (4-methoxyphenacyl) piperazine, |
| IV-15 | $N^1$-phenacyl-$N^4$-[(2-hydroxy) phenylacetyl] piperazine, |
| IV-16 | $N^1$-(4-methoxyphenacyl)-$N^4$-[(2-hydroxy) phenylacetyl] piperazine, |
| IV-17 | $N^1$-(1-benzoylethyl)-$N^4$-[2-hydroxy-2-(4-chlorophenyl)acetyl] piperazine, |
| IV-18 | $N^1$-(1-benzoylethyl)-$N^4$-[(2-hydroxy) phenylacetyl] piperazine, |
| IV-19 | $N^1$-phenacyl-$N^4$-[2-hydroxy-2-(4-chlorophenyl) acetyl] piperazine, |
| IV-20 | $N^1$-phenacyl-$N^4$-[1-(5-chloro-6-methoxy-2-naphthoyl) ethyl]piperazine, |
| IV-21 | N1-[2-(benzylamino)-2-oxo-ethyl]-$N^4$-cinnamyl piperazine, |
| IV-22 | $N^1$-phenacyl-$N^4$-(2,4-difluorobenzylsulfonyl) piperazine, |
| IV-23 | $N^1$-phenacyl-$N^4$-[2-(benzylamino)-2-oxo-ethyl] piperazine |
| IV-24 | $N^1$-phenacyl-$N^4$-[2-(phenylamino)-2-oxo-ethyl] piperazine |
| IV-25 | $N^1$,$N^4$-di[2-(benzylamino)-2-oxo-ethyl] piperazine |
| IV-26 | $N^1$-(1-benzoylethyl)-$N^4$-[2-(benzylamino)-2-oxo-ethyl] piperazine |
| IV-27 | $N^1$-(4-chlorophenacyl)-$N^4$-[2-(benzylamino)-2-oxo-ethyl] piperazine |
| IV-28 | $N^1$-(4-methoxyphenacyl)-$N^4$-[2-(benzylamino)-2-oxo-ethyl] piperazine |
| IV-29 | $N^1$-phenacyl-$N^4$-[2-(R-1-phenylethanamino)-2-oxo-ethyl] piperazine |
| IV-30 | $N^1$-phenacyl-$N^4$-[2-(4-methoxybenzylamino)-2-oxo-ethyl] piperazine |
| IV-31 | $N^1$-phenacyl-$N^4$-[2-(2-pyridylmethylamino)-2-oxo-ethyl] piperazine |
| IV-32 | $N^1$-phenacyl-$N^4$-[2-(3,4-methylenedioxybenzylamino)-2-oxo-ethyl] piperazine |
| IV-33 | $N^1$-[1-(5-chloro-6-methoxy-2-naphthoyl)ethyl]-$N^4$-[2-(benzylamino)-2-oxo-ethyl] piperazine |
| IV-34 | $N^1$-benzoyl-$N^4$-(2-phenylethyl-2-ol) piperazine |
| IV-35 | $N^1$-(4-nitrobenzoyl)-$N^4$-(2-phenylethyl-2-ol) piperazine |
| IV-36 | $N^1$-phenacyl-$N^4$-(2-phenylethyl-2-ol) piperazine |
| IV-37 | $N^1$-[2-(benzylamino)-2-oxo-ethyl]-$N^4$-(2-phenylethyl-2-ol) piperazine |
| IV-38 | $N^1$-(4-methoxyphenacyl)-$N^4$-(3-phenylpropyl-3-ol) piperazine |
| IV-39 | $N^1$-(4-chlorophenacyl)-$N^4$-(2-phenylethyl-2-ol) piperazine |
| IV-40 | $N^1$-(4-methoxyphenacyl)-$N^4$-(2-phenylethyl-2-ol) piperazine |
| IV-41 | $N^1$-(1-benzoylethyl)-$N^4$-(2-phenylethyl-2-ol) piperazine |
| IV-42 | $N^1$-[2-(4-acetamidophenyl)-2-oxo-ethyl]-$N^4$-(2-phenylethyl-2-ol) piperazine |
| IV-43 | $N^1$-(2-hydroxy-1-oxo-2-phenylethyl)-$N^4$-(phenylpropane-2-yl-3-ol) piperazine |
| IV-44 | $N^1$-(S-2-hydroxy-1-oxo-2-phenylethyl)-$N^4$-(1-benzoylethyl) piperazine |
| IV-45 | $N^1$-phenacyl-$N^4$-(3-fluorophenylmethylsulfonyl) piperazine |
| IV-46 | $N^1$-phenacyl-$N^4$-(3-bromophenylmethylsulfonyl) piperazine |
| IV-47 | $N^1$-phenacyl-$N^4$-(3-iodophenylmethylsulfonyl) piperazine |
| IV-48 | $N^1$-phenacyl-$N^4$-(3-cyanophenylmethylsulfonyl) piperazine |
| IV-49 | $N^1$-[1-(5-chloro-6-methoxy-2-naphthoyl)ethyl]-$N^4$-[2-(1-phenylethanamino)-2-oxo-ethyl] piperazine |
| IV-50 | $N^1$-phenacyl-$N^4$-(2-fluorobenzylsulfonyl) piperazine |
| IV-51 | $N^1$-phenacyl-$N^4$-(2,5-difluorobenzylsufonyl) piperazine |
| IV-52 | $N^1$-phenacyl-$N^4$-(2,5-dichlorobenzylsulfonyl) piperazine |
| IV-53 | $N^1$-phenacyl-$N^4$-(4-phenoxybenzylsulfonyl) piperazine |
| IV-54 | $N^1$-phenacyl-$N^4$-[2-(benzenesulfonylmethyl)benzylsulfonyl] piperazine |
| IV-55 | $N^1$-phenacyl-$N^4$-(4-trifluoromethylbenzylsulfonyl) piperazine |
| IV-56 | $N^1$-phenacyl-$N^4$-(4-phenylbenzylsulfonyl) piperazine |
| IV-57 | $N^1$-phenacyl-$N^4$-(3-methoxybenzylsulfonyl) piperazine |
| IV-58 | $N^1$-phenacyl-$N^4$-[4-(2-cyanophenyl)benzylsulfonyl] piperazine |
| IV-59 | $N^1$-[2-(benzylamino)-2-oxo-ethyl]-$N^4$-(2,4-difluorobenzylsulfonyl) piperazine |
| IV-60 | $N^1$-[2-(benzylamino)-2-oxo-ethyl]-$N^4$-(2,5-difluorophenylmethylsulfonyl) piperazine |

-continued

| Code | Chemical Name |
|---|---|
| IV-61 | $N^1$-[2-(benzylamino)-2-oxo-ethyl]-$N^4$-[4-(2-cyanophenyl)benzylsulfonyl] piperazine |
| IV-62 | $N^1$-[2-(benzylamino)-2-oxo-ethyl]-$N^4$-[2-(benzenesulfonylmethyl)benzyl sulfonyl] piperazine |
| IV-63 | $N^1$-[2-(benzylamino)-2-oxo-ethyl]-$N^4$-(3,4-dichlorobenzylsulfonyl) piperazine |
| IV-64 | $N^1$-[2-(benzylamino)-2-oxo-ethyl]-$N^4$-(4-nitrobenzylsulfonyl) piperazine |
| IV-65 | $N^1$-[1-(5-chloro-6-methoxy-2-naphthoyl)ethyl]-$N^4$-[2-(benzylamino)-2-oxo-ethyl] piperazine |
| IV-66 | $N^1$-[1-(5-chloro-6-methoxy-2-naphthoyl)ethyl]-$N^4$-(4-methoxyphenacyl) piperazine |
| IV-67 | $N^1$-[1-(5-chloro-6-methoxy-2-naphthoyl)ethyl]-$N^4$-(4-Chlorophenacyl) piperazine |
| IV-68 | $N^1$-[1-(5-chloro-6-methoxy-2-naphthoyl)ethyl]-$N^4$-(4-methylsulfonylphenacyl) piperazine |
| IV-69 | $N^1$-[2-(benzylamino)-2-oxo-ethyl]-$N^4$-[1-(5-chloro-6-methoxyl-naphthalen-2-yl)-propane-2-yl-1-ol] piperazine |
| IV-70 | $N^1$-(4-chlorophenacyl)-$N^4$-[1-(5-chloro-6-methoxyl-naphthalen-2-yl)-propane-2-yl-1-ol] piperazine |

Particularly preferable is $N^1$-phenacyl-$N^4$-[2-(benzylamino)-2-oxo-ethyl]piperazine.

Their structures are shown in Table 1.

TABLE 1

The Structure of Compounds

| Code | $Ar_1$ | $Ar_2$ | $R_1$ | $R_2$ | $R_3$ | X | $m_1$ | $m_2$ | n |
|---|---|---|---|---|---|---|---|---|---|
| IV-1 | Ph | Ph | H | 0 | 0 | C=O | 1 | 0 | 0 |
| IV-2 | Ph | Ph | H | H | 0 | C=O | 1 | 0 | 1 |
| IV-3 | $NO_2$-C$_6$H$_4$- | Ph | 0 | H | 0 | C=O | 1 | 0 | 0 |
| IV-4 | Ph | Ph | $CH_3$ | 0 | $OCOCH_3$ | C=O | 0 | 1 | 1 |
| IV-5 | Ph | Cl-C$_6$H$_4$- | H | H | 0 | C=O | 1 | 0 | 1 |
| IV-6 | -C$_6$H$_4$-Cl | Cl-C$_6$H$_4$- | H | H | 0 | C=O | 1 | 0 | 1 |
| IV-7 | naphthyl | Ph | H | H | 0 | C=O | 1 | 0 | 1 |
| VI-8 | Ph | Ph | $CH_3$ | H | 0 | C=O | 1 | 0 | 1 |
| IV-9 | Ph | C$_6$H$_4$-$OCH_3$ | H | H | 0 | C=O | 1 | 0 | 1 |
| IV-10 | Ph | Ph | $CH_3$ | $CH_3$ | 0 | C=O | 1 | 0 | 1 |
| IV-11 | Ph | C$_6$H$_4$-$NO_2$ | H | H | 0 | C=O | 1 | 0 | 1 |
| IV-12 | Ph | Ph | H | 0 | H | C=O | 0 | 1 | 1 |
| IV-13 | Ph | Ph | H | H | 0 | C=O | 1 | 0 | 2 |

TABLE 1-continued
The Structure of Compounds
| Code | Ar₁ | Ar₂ | R₁ | R₂ | R₃ | X | m₁ | m₂ | n |
|---|---|---|---|---|---|---|---|---|---|
| IV-14 | 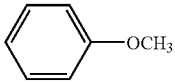 | 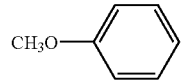 | H | H | 0 | C=O | 1 | 0 | 1 |
| IV-15 | Ph | Ph | H | 0 | OH | C=O | 0 | 1 | 1 |
| IV-16 | 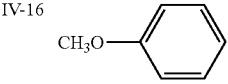 | Ph | H | 0 | OH | C=O | 0 | 1 | 1 |
| IV-17 | Ph | 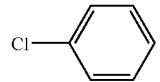 | CH₃ | 0 | OH | C=O | 0 | 1 | 1 |
| IV-18 | Ph | Ph | CH₃ | 0 | OH | C=O | 0 | 1 | 1 |
| IV-19 | Ph | 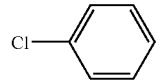 | H | 0 | OH | C=O | 0 | 1 | 1 |
| IV-20 | Ph | 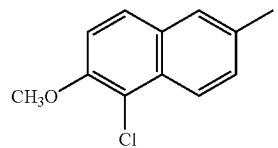 | H | CH₃ | 0 | CO | 1 | 0 | 1 |
| IV-21 | 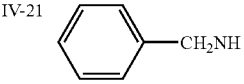 | Ph | H | H | 0 | CH=CH | 1 | 0 | 1 |
| IV-22 | Ph | 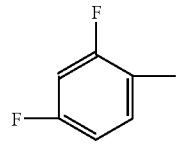 | H | 0 | H | SO₂ | 0 | 1 | 1 |
| IV-23 | Ph | Ph | H | H | H | CONH | 1 | 1 | 1 |
| IV-24 | Ph | Ph | H | H | 0 | CONH | 1 | 0 | 1 |
| IV-25 | 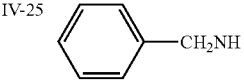 | Ph | H | H | H | CONH | 1 | 1 | 1 |
| IV-26 | Ph | Ph | CH₃ | H | H | CONH | 1 | 1 | 1 |
| IV-27 | 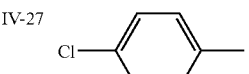 | Ph | H | H | H | CONH | 1 | 1 | 1 |
| IV-28 | 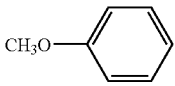 | Ph | H | H | H | CONH | 1 | 1 | 1 |
| IV-29 | Ph | Ph | H | H | CH₃ | CONH | 1 | 1 | 1 |
| IV-30 | Ph | 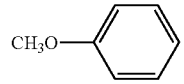 | H | H | H | CONH | 1 |  | 1 |

TABLE 1-continued

The Structure of Compounds

| Code | Ar$_1$ | Ar$_2$ | R$_1$ | R$_2$ | R$_3$ | X | m$_1$ | m$_2$ | n |
|---|---|---|---|---|---|---|---|---|---|
| IV-31 | Ph | pyridyl | H | H | H | CONH | 1 | 1 | 1 |
| IV-32 | Ph | benzo[1,3]dioxolyl | H | H | H | CONH | 1 | 1 | 1 |
| IV-33 | 2-CH$_3$O-1-Cl-naphthyl | Ph | CH$_3$ | H | H | CONH | 1 | 1 | 1 |
| IV-34 | Ph | Ph | 0 | H | 0 | CHOH | 1 | 0 | 0 |
| IV-35 | 4-NO$_2$-phenyl | Ph | 0 | H | 0 | CHOH | 1 | 0 | 0 |
| IV-36 | Ph | Ph | H | H | 0 | CHOH | 1 | 0 | 1 |
| IV-37 | PhCH$_2$NH- | Ph | H | H | 0 | CHOH | 1 | 0 | 1 |
| IV-38 | CH$_3$O-phenyl | Ph | H | H | 0 | CHOH | 2 | 0 | 1 |
| IV-39 | Cl-phenyl | Ph | H | H | 0 | CHOH | 1 | 0 | 1 |
| IV-40 | CH$_3$O-phenyl | Ph | H | H | 0 | CHOH | 1 | 0 | 1 |
| IV-41 | Ph | Ph | CH$_3$ | H | 0 | CHOH | 1 | 0 | 1 |
| IV-42 | 4-NHCOCH$_3$-phenyl | Ph | H | H | 0 | CHOH | 1 | 0 | 1 |
| IV-43 | Ph-CH(OH)- | Ph | 0 | CH$_3$ | 0 | CHOH | 1 | 0 | 0 |
| IV-44 | Ph-CH(OH)- | Ph | 0 | CH$_3$ | 0 | C=O | 1 | 0 | 0 |
| IV-45 | Ph | 4-F-phenyl | H | 0 | H | —SO$_2$— | 0 | 1 | 1 |
| IV-46 | Ph | Br-phenyl | H | 0 | H | —SO$_2$— | 0 | 1 | 1 |

TABLE 1-continued

The Structure of Compounds

| Code | Ar₁ | Ar₂ | R₁ | R₂ | R₃ | X | m₁ | m₂ | n |
|------|-----|-----|-----|-----|-----|------|-----|-----|---|
| IV-47 | Ph | 3-I-C₆H₄– | H | 0 | H | —SO₂— | 0 | 1 | 1 |
| IV-48 | Ph | 3-NC-C₆H₄– | H | 0 | H | —SO₂— | 0 | 1 | 1 |
| IV-49 | 1-Cl-2-CH₃O-6-naphthyl | Ph | CH₃ | H | CH₃ | CHOH | 1 | 1 | 1 |
| IV-50 | Ph | 2-F-C₆H₄– | H | 0 | H | —SO₂— | 0 | 1 | 1 |
| IV-51 | Ph | 2,5-F₂-C₆H₃– | H | 0 | H | —SO₂— | 0 | 1 | 1 |
| IV-52 | Ph | 2,5-Cl₂-C₆H₃– | H | 0 | H | —SO₂— | 0 | 1 | 1 |
| IV-53 | Ph | 4-PhO-C₆H₄– | H | 0 | H | —SO₂— | 0 | 1 | 1 |
| IV-54 | Ph | 2-(PhSO₂CH₂)-C₆H₄– | H | 0 | H | —SO₂— | 0 | 1 | 1 |
| IV-55 | PH | 4-CF₃-C₆H₄– | H | 0 | H | —SO₂— | 0 | 1 | 1 |
| IV-56 | Ph | 4-Ph-C₆H₄– | H | 0 | H | —SO₂— | 0 | 1 | 1 |
| IV-57 | Ph | 3-CH₃O-C₆H₄– | H | 0 | H | —SO₂— | 0 | 1 | 1 |

TABLE 1-continued

The Structure of Compounds

| Code | Ar$_1$ | Ar$_2$ | R$_1$ | R$_2$ | R$_3$ | X | m$_1$ | m$_2$ | n |
|---|---|---|---|---|---|---|---|---|---|
| IV-58 | Ph | 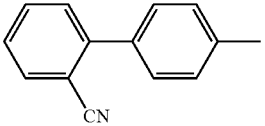 2-biphenyl-CN | H | 0 | H | —SO$_2$— | 0 | 1 | 1 |
| IV-59 | 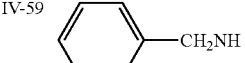 PhCH$_2$NH | 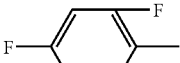 2,4-difluorophenyl | H | 0 | H | —SO$_2$— | 0 | 1 | 1 |
| IV-60 | 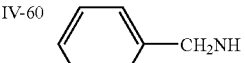 PhCH$_2$NH | 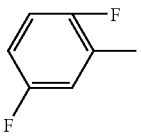 2,5-difluorophenyl | H | 0 | H | —SO$_2$— | 0 | 1 | 1 |
| IV-61 | 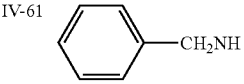 PhCH$_2$NH | 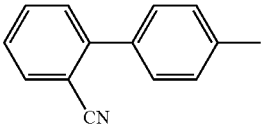 2-biphenyl-CN | H | 0 | H | —SO$_2$— | 1 | 1 | 1 |
| IV-62 | 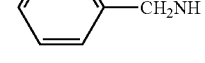 PhCH$_2$NH | 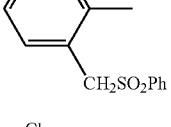 2-(CH$_2$SO$_2$Ph)phenyl | H | 0 | H | —SO$_2$— | 1 | 1 | 1 |
| IV-63 | 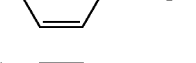 PhCH$_2$NH | 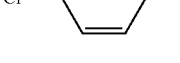 3,4-dichlorophenyl | H | 0 | H | —SO$_2$— | 0 | 1 | 1 |
| IV-64 | 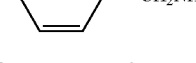 PhCH$_2$NH | 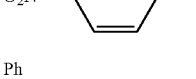 4-nitrophenyl | H | 0 | H | —SO$_2$— | 0 | 1 | 1 |
| IV-65 | 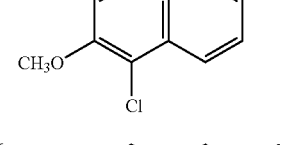 1-Cl-2-CH$_3$O-naphthyl | Ph | CH$_3$ | H | H | CONH | 1 | 1 | 1 |
| IV-66 | 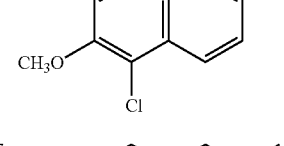 1-Cl-2-CH$_3$O-naphthyl | 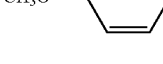 CH$_3$O-phenyl | CH$_3$ | H | 0 | CO | 1 | 0 | 1 |
| IV-67 | 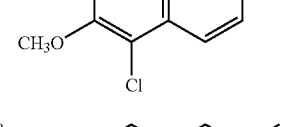 1-Cl-2-CH$_3$O-naphthyl | 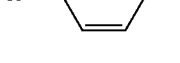 4-Cl-phenyl | CH$_3$ | H | 0 | CO | 1 | 0 | 1 |
| IV-68 | 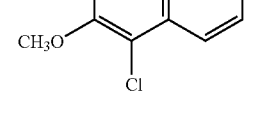 1-Cl-2-CH$_3$O-naphthyl | 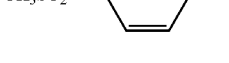 4-(CH$_3$SO$_2$)phenyl | CH$_3$ | H | 0 | CO | 1 | 0 | 1 |

TABLE 1-continued

The Structure of Compounds

| Code | Ar₁ | Ar₂ | $R_1$ | $R_2$ | $R_3$ | X | $m_1$ | $m_2$ | n |
|---|---|---|---|---|---|---|---|---|---|
| IV-69 | (phenyl)-CH₂NH- | 6-methyl-2-methoxy-1-chloro-naphthalen-yl | H | CH₃ | 0 | CHOH | 1 | 0 | 1 |
| IV-70 | 4-Cl-phenyl-CH₂- | 6-methyl-2-methoxy-1-chloro-naphthalen-yl | H | CH₃ | 0 | CHOH | 1 | 0 | 1 |

The above-mentioned compounds can be prepared by the following two synthetic routes.

Synthetic route 1:

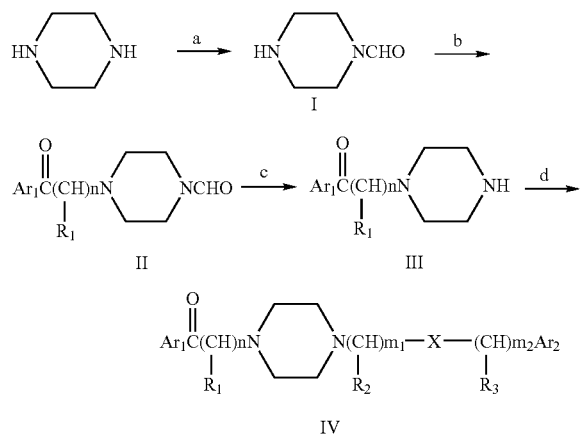

X = —CHOH—, —CO—, —CONH— or —SO₂—, etc.

Synthetic route 2:

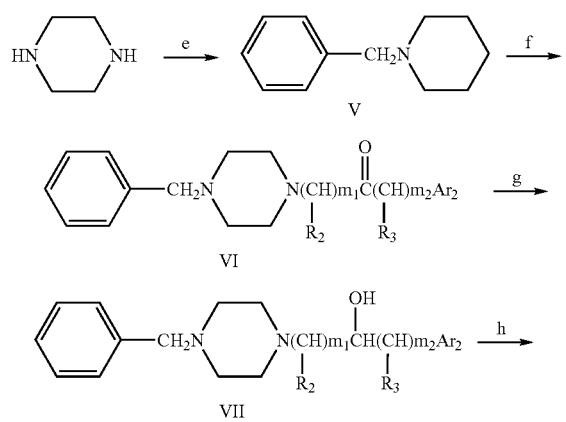

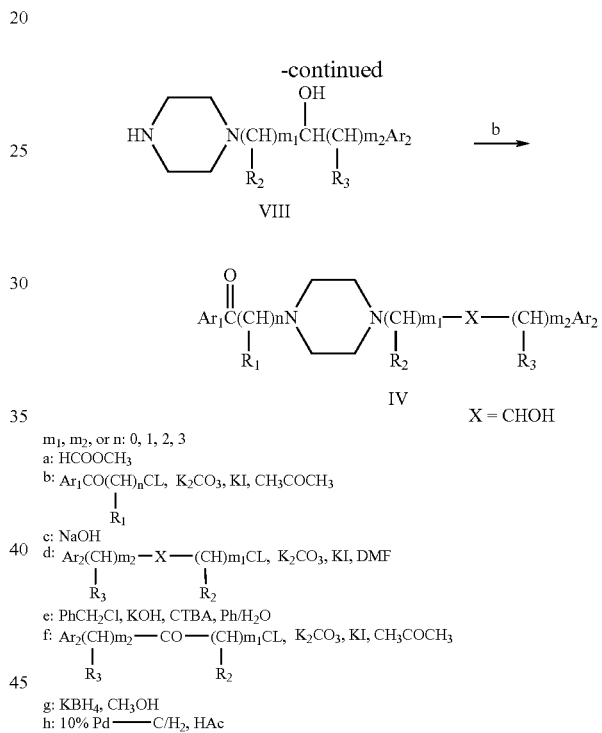

$m_1$, $m_2$, or n: 0, 1, 2, 3 a: HCOOCH₃ b: Ar₁CO(CH)ₙCL, K₂CO₃, KI, CH₃COCH₃
   |
   R₁ c: NaOH d: Ar₂(CH)m₂—X—(CH)m₁CL, K₂CO₃, KI, DMF
   |           |
   R₃          R₂ e: PhCH₂Cl, KOH, CTBA, Ph/H₂O f: Ar₂(CH)m₂—CO—(CH)m₁CL, K₂CO₃, KI, CH₃COCH₃
   |              |
   R₃             R₂ g: KBH₄, CH₃OH h: 10% Pd——C/H₂, HAc

Piperazine is used as a starting material to prepare the above-mentioned compounds. The N atom of the piperazine ring is protected by formyl group first, and then alkylated, finally the formyl group is removed by alkaline hydrolysis to obtain compound (III) with a higher purity and yield. The total yield of three procedures is about 40%. Compound (III), an important intermediate, is alkylated at $N^4$ with corresponding halide to obtain compound (IV). When using K₂CO₃/DMF, the reaction can take place at room temperature, and the yield is about 80%. If using K₂CO₃/CH₃COCH₃, NaHCO₃/C₂H₅OH, or Et₃N/CHCl₃ as reaction systems, the reaction it needs reflux for about 8-24 h, and the color of the reaction mix will deepen as time passes. This will reduce the quality and yield of the products. Compounds IV-1 to IV-33 and IV-44 to IV-68 are obtained by the above mentioned procedures.

The goal compounds IV-34 to IV-43, IV-69 and IV-70 contain difunctional carbonyl and hydroxyl groups. N-benzyl piperazine is reacted with corresponding bromo-aralkyl ketones to obtain $N_1$, $N_4$-disubstituted compound (VI). Compound (VI) is reduced by $KBH_4$ and then hydrogenated by 10% Pd—C at 70° C. in HAC to give compound (VIII). Reduction and hydrogenation of compound (VI) also can be carried out in one step through step h. But when the activity of carbonyl is weak, there are still many unreduced carbonyl materials left. Therefore, carbonyl group should be first reduced by $KBH_4$ before hydrogenation in order to obtain compound (VIII) with sufficient purity.

The goal compounds IV-34 to IV-43, IV-69 and IV-70 can be obtained by using a key intermediate compound (VIII) with halogen-aralkyl ketones.

Halogenated aralkyl formyl alkyl compounds in steps b, d and f can be obtained commercially, but can also be prepared with bromine or copper bromide corresponding aralkyl ketones using methods known in the literature.

The inventors discovered that aralkyl formyl alkyl piperazine derivatives in the present invention are effective against ischemic cerebral apoplexy, and especially, they have therapeutic activities for acute ischemia cerebral infarction. Also, these compounds have neuroprotective activities after ischemic cerebral apoplexy. Therefore, the compounds from this invention can be used to develop acute therapeutic agents against ischemia cerebral infraction and a neuroprotective agent after ischemic cerebral apoplexy.

Using well-known methods in the art an effective amount of the compounds from this invention can be combined with any pharmaceutically acceptable carriers to prepare clinical solid formulations, such as tablets, powders, capsules or injections, etc.

The carriers mentioned above represent the routine pharmaceutical carriers, such as dilutents, excipents (water, etc), filling materials (starch, sugar, etc), adhesives (fibrin derivatives, gelatin, polyvinyl, pyrrolidone, etc), wetting agents (glycerin, etc), surface active agents (cetanol, etc), disintegrants (calcium carbonate, etc) and lubricants (talc powder, calcium stearate, magnesium stearate, etc).

According to claims of this invention, the content of the compound is about 0.1-99.5% in the tablet, powder, capsule or injection.

The inventive compounds can be taken by the patients in the form of oral administration, injection and so on. For oral administration, the compounds can be prepared into regular solid formulations, such as tablets, powders or capsules. For injection, they can be prepared into liquid form.

The dosage of these compounds could be regulated according to the age and the weight of the patients, and specific cases of diseases. Daily whole dosage can be 2-50 mg/kg (po) or 1-20 mg/kg (iv).

The compounds in this invention have showed potent prevention and therapeutic actions on global cerebral ischemia and focal cerebral ischemia on animals. Their therapeutic effects are much better than previously known related drugs.

The inventors also discovered that the inventive compounds have low toxicity levels and fewer side effects for the central nervous system.

EXAMPLES

General Preparation 1

N-aralkyl formyl alkyl piperazine dihydrochloride (III)

Figure 1:
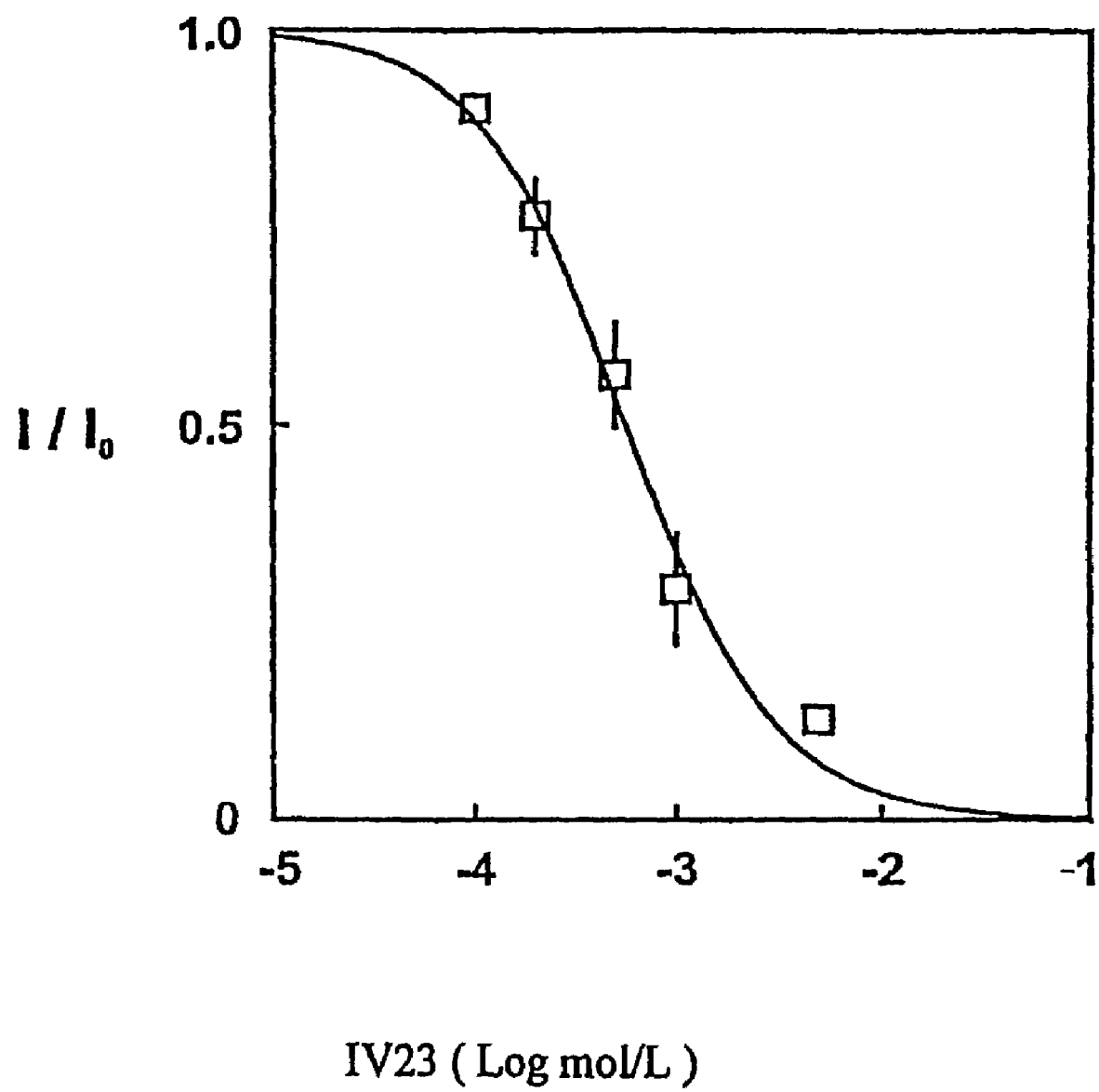
FIG. 1. The curve of IV23 restraining the current induced by 100 μM NMDA

A mixture of piperazine (258 g, 3 mol) and methyl formate (180 g, 3 mol) was refluxed for 8 h, the excessive piperazine was removed in vacuo, and collected at 130-134° C./8-10 mm-Hg 240 g of N-formyl piperazine was obtained (70%).

A mixture of the above product (310 mmol), aralkyl formylalkyl halogen (372 mmol), $K_2CO_3$ (465 mmol) and KI (30 mmol) in 320 ml of acetone was refluxed for 8-16 h, filtered off; the filtrate was evaporated in vacuo. 5% NaOH (350 ml) was added to the residue, after refluxed for 10 h, and then adjusted to a ph of 8 by 6 N HCl, extracted with $CHCl_3$ (200 ml×3). The combined organic layer was washed with 50 ml of water and saline, dried ($MgSO_4$), filtered and evaporated. The residue was dissolved in 20 ml of ethanol and then adjusted to a ph of 3 by $HCl/C_2H_5OH$ (5N), the resulting precipitate was recrystallized from aqueous ethanol to obtain N-aralkyl formylalkyl piperazine dihydrochloride (III) (55-60%).

General Preparation 2

$N^1$-aralkylformylalkyl-$N^4$-aralkyl piperazine dihydrochloride (IV)

A mixture of compound (III) (10 mmol), aralkyl halogen (12 mmol), KI(1 mmol) and $K_2CO_3$(35 mmol) in DMF(50 ml) was stirred at 25° C.-60° C. for 8-12 h, filtrated, and then evaporated to dryness, 50 ml of water and EtOAc (100 ml×3) were added to the residue, the organic layer was washed with saline, dried ($MgSO_4$). Filtered and evaporated, the residue was dissolved by 30 ml of ethanol and then adjusted to a PH of 2 by $HCl/C_2H_5OH$ (5N); the resulting precipitate was recrystallized from ethanol or $CH_3OH$ to obtain the title product (IV)(60-85%).

General Preparation 3

$N^1$-benzyl-$N^4$-aralkyl formyl alkyl piperazine dihydro chloride (VI)

A mixture of piperazine (350 mmol), KOH (100 mmol) and hexadecyl-trimethyl ammonium bromide (CTAB, 1 mmol) in water (18 ml) was heated to get a solution. Thereafter, benzyl chloride (100 mmol) in 140 ml of benzene was added to the solution dropwise at 70° C., and refluxed for 1 h. The organic layer was washed with water and saline, dried ($MgSO_4$), filtered and evaporated, the residue was dissolved by 50 ml of ethanol and adjusted to a PH of 2 by $HCl/C_2H_5OH$ (5N), the resulting precipitate was recrystallized from ethanol to obtain N-benzyl piperazine dihydrochloride (55-86%).

A mixture of N-benzyl piperazine dihydrochloride (20 mmol), aryl formyl alkyl halide (24 mmol), $K_2CO_3$ (7 mmol) and KI (2 mmol) in 100 ml of acetone was treated according to the general preparation 2 to obtain compound (VI) (65-75%).

General Preparation 4

$N^1$-benzyl-$N^4$-aralkanol piperazine dihydrochloride (VII)

To a mixture of compound (VI) (3.5 mmol) and $KHCO_3$ (8.75 mmol) in methanol (60 ml) was added $KBH_4$ (14 mmol), stirred at room temperature for 2 h, and then at 50° C. for 1 h, adjusted to a PH of 3 by 1N aqueous NaOH and then filtered. The filtrate was extracted with EtOAC (40 ml×3), washed with saline, evaporated to dryness, which was dissolved in 20 ml of ethanol, and adjusted to a PH of 2 by $HCl/C_2H_5OH$ (5N), the resulting precipitate was recrystallized from ethanol to obtain the title compound (60-80%).

General Preparation 5

N-aralkanol piperazine dihydrochloride (VIII)

To a mixture of the above compound (VII) in HAc (60 ml) was added 10% Pd—C (0.4 g), stirred with $H_2$ at 70° C. for 4 h, filtered off and evaporated to dryness, which was dissolved in 10 ml of ethanol, and adjusted to a PH of 2 by $HCl/C_2H_5OH$ (5N), the resulting precipitate was recrystallized from ethanol to obtain the title compound (80-85%).

Example 1

(IV-2) $N^1,N^4$-diphenacyl piperazine dihydrochloride

A mixture of piperazine (2 g, 23.22 mmol), 2-chloro-1-phenylethanone (7.89 g) and $K_2CO_3$ (8 g, 58.08 mmol) in 30 ml of DMF was stirred at 50° C. for 8 h, and treated according to the general preparation 2 to give 6.6 g of compound (IV-2) (72%), mp 258-259° C., $M^+$ 322.

Elemental analysis (found): $C_{20}H_{22}N_2O_2.2HCl$ (C, 60.91%; H, 6.40%; N, 7.26%). $^1HNMR(DMSO-d_6)$: δ3.46 (m, 8H, piperazine-H), 5.09(s, 4H, $2COCH_2N$), 7.59-8.02 (m, 10H, ArH).

Example 2

(IV-7) $N^1$-(2-naphthoylmethyl)-$N^4$-phenacyl-piperazine dihydrochloride

A mixture of N-formyl piperazine (20 g, 175 mmol), 2-chloro-1-phenylethanone (32.5 g, 210 mmol) and $K_2CO_3$ (36 g, 262 mmol) in 180 ml of acetone was treated according to the general preparation 1 to give N-phenacyl piperazine dihydrochloride, 28 g (57%), mp 246-8° C. (dec).

A mixture of 2-bromo-1-(naphthalen-2-yl)ethanone (0.95 g, 3.8 mmol), N-phenacyl piperazine dihydrochloride (0.89 g, 3.2 mmol) and $K_2CO_3$ (1.56 g, 11.2 mmol) in 30 ml of DMF was stirred at 50° C. for 10 h, and treated according to the general preparation 2 to give compound (IV-7), 0.88 g (60.69%), mp 236-237° C., $M^+$ 373.

Elemental analysis (found): $C_{24}H_{24}N_2O_2.2HCl.1/2H_2O$. (C, 63.41%; H, 5.87%; N, 5.96%). $^1HNMR(DMSO-d_6/D_2O)$:δ3.56 (m, 8H, piperazine-H), 4.90(s, 2H, $PhCOCH_2$), 5.03(s, 2H), 7.54-8.63 (m, 12H, ArH).

Example 3

(IV-8) $N^1$-(1-benzoylethyl)-$N^4$-phenacyl-piperazine dihydrochloride

A mixture of 2-bromo-1-phenylpropan-1-one (3 mmol), N-phenacyl piperazine dihydrochloride (2.5 mmol) and $K_2CO_3$ (8.75 mmol) in 30 ml of DMF was treated according to the general preparation 2 to give compound (IV-8), 0.64 g (62%), mp 236-238° C., $M^+$ 336.

Elemental analysis (found): $C_{21}H_{24}N_2O_2.2HCl$ (C, 62.02%; H, 6.64%; N, 6.57%). $^1HNMR(DMSO-d_6)$:δ1.73 (d, J=6.0, 3H, $COCH(CH_3)N$), 3.56(m, 8H, piperazine-H), 5.44 (m, br, 1H, COCHN), 4.90(s, 2H, $PhCOCH_2$), 7.55-8.05(m, 10H, ArH).

Example 4

(IV-9) $N^1$-phenacyl-$N^4$-(4-methoxyphenacyl)piperazine dihydrochloride

A mixture of 2-chloro-1-(4-methoxyphenyl)ethanone (3 mmol), N-phenacyl piperazine dihydrochloride (3 mmol) and $K_2CO_3$ (10 mmol) in 30 ml of DMF was treated according to the general preparation 2 to give compound (IV-9), 0.68 g (62%), mp 226-228° C., $M^+$ 352.

Elemental analysis (found): $C_{21}H_{24}N_2O_3.2HCl.H_2O$ (C, 57.13%; H, 6.10%; N, 6.23%). $^1HNMR(DMSO-d_6)$: δ2.05 (s, 3H, $CH_3O$), 3.56(m, 8H, piperazine-H), 5.07-5.12 (m, 4H, $COCH_2N$), 7.53-8.04(m, 9H, ArH).

Example 5

(IV-10) $N^1,N^4$-di(1-benzoylethyl)piperazine dihydrochloride

A mixture of piperazine (1.5 mmol), 2-bromo-1-phenylpropan-1-one (3 mmol), and $K_2CO_3$ (8.75 mmol) in 30 ml of DMF was stirred at 50° C. for 8 h, then was treated according to the general preparation 2 to give compound (IV-10), 0.55 g (85%), mp 240-242° C., $M^+$ 350.

Elemental analysis (found): $C_{22}H_{26}N_2O_2.2HCl.1/2H_2O$ (C, 61.40%; H, 6.74%; N, 6.64%). $^1HNMR(DMSO-d_6)$: δ1.73(d, J=6.0, 6H, $2COCH(CH_3)N$), 3.56(m, 8H, piperazine-H), 5.44 (m, br, 2H, COCHN), 7.53-8.06(m, 10H, ArH).

Example 6

(IV-11) $N^1$-phenacyl-$N^4$-(4-nitrophenacyl)piperazine dihydrochloride

A mixture of 2-chloro-1-(4-nitrophenyl)ethanone (3.2 mmol), N-phenacyl piperazine dihydrochloride (3 mmol), and $K_2CO_3$ (9 mmol) in 30 ml of DMF was treated according to the general preparation 2 to give compound (IV-11), 0.71 g (61%), mp 204-205° C., $M^+$ 367.

Elemental analysis (found): $C_{20}H_{21}N_3O_4.2HCl.3/2H_2O$ (C, 51.71%; H, 5.80%; N, 8.99%). $^1HNMR (DMSO-d_6)$: δ 3.56(m, 8H, piperazine-H), 5.09-5.21(m, 4H, $2COCH_2N$), 7.55-9.05 (m, 9H, ArH).

Example 7

(IV-13) $N^1$-(1-benzoylethyl)-$N^4$-phenacyl piperazine dihydrochloride

A mixture of 3-bromo-1-phenylpropan-1-one (1.5 g, 8.9 mmol), N-phenacyl piperazine dihydrochloride (2.05 g, 7.4 mmol) and $K_2CO_3$ (21.75 mmol) in 30 ml of DMF was treated according to the general preparation 2 to give compound (IV-13), 0.64 g (76%), mp 204-205° C., $M^+$ 336.

Elemental analysis (found): $C_{21}H_{24}N_2O_2 \cdot 2HCl$ (C, 61.17%; H, 6.37%; N, 6.48%). $^1$HNMR(DMSO-$d_6$): δ 3.37-3.41 (m, 4H, NCH$_2$CH$_2$CO), 3.55 (m, 8H, piperazine-H), 5.15 (s, 2H, COCH$_2$N), 7.43-7.95 (m, 10H, ArH).

Example 8

(IV-18) $N^1$-(1-benzoylethyl)-$N^4$-[(2-hydroxy)phenylacetyl]piperazine hydrochloride A mixture of 2-bromo-1-phenylpropan-1-one (3 mmol), N-(2-hydroxy-phenyl acetyl)piperazine hydrochloride (2.5 mmol) and $K_2CO_3$ (8.75 mmol) in 30 ml of DMF was treated according to the general preparation 2 to give compound (IV-18), 0.65 g (67%), $M^+$ 353.

Elemental analysis (found): $C_{21}H_{24}N_2O_3 \cdot HCl$ (C, 64.80%; H, 6.42%; N, 7.20%). $^1$HNMR(DMSO-$d_6$): δ1.73 (d, J=6.0, 3H, COCH(CH$_3$)N), 3.56 (m, 8H, piperazine-H), 4.77 (s, 1H, PhCHCO), 5.44 (m, br, 1H, COCHN), 7.55-8.05(m, 10H, ArH).

Example 9

(IV-20) $N^1$-phenacyl-$N^4$-[1-(5-chloro-6-methoxy-2-naphthoyl)ethyl]piperazine dihydrochloride A mixture of 2-bromo-1-(5-chloro-6-methoxynaphthalen-2-yl)propan-1-one (3.8 mmol), N-phenacyl piperazine dihydrochloride (0.89 g, 3.2 mmol) and $K_2CO_3$ (1.56 g, 11.2 mmol) in 30 ml of DMF are stirred at 50° C. for 10 h, then was treated according to the general preparation 2 to give compound(IV-19), 1.09 g (61%), $M^+$ 451.

Elemental analysis (found): $C_{26}H_{27}ClN_2O_3 \cdot 2HCl \cdot 2H_2O$. $^1$HNMR(DMSO-$d_6$/$D_2O$): δ 1.70 (d, J=6.0, 3H, COCH(CH$_3$)N), 3.56(m, 8H, piperazine-H), 4.90(s, 2H, PhCOCH$_2$), 5.41(m, br, 1H, COCHN), 8.64-9.11(m, 4H, ArH).

Example 10

(IV-21) $N^1$-[2-(benzylamino)-2-oxo-ethyl]-$N^4$-cinnamyl piperazine dihydrochloride A mixture of N-benzyl-2-chloroacetamide (3.9 mmol), trans-1-cinnamylpiperazine dihydrochloride (5.1 mmol, prepared by using the general preparation 1) and $K_2CO_3$ (8.5 mmol) in 30 ml of DMF was treated according to the general preparation 2 to give compound(IV-21), 0.75 g (69%), mp 226-228° C., $M^+$ 349.

Elemental analysis (found): $C_{22}H_{27}N_3O \cdot 2HCl \cdot H_2O$(C, 59.97% H, 7.02% N, 9.65%). $^1$HNMR(DMSO-$d_6$):δ3.46-3.57(m, 10H, piperazine-H), 3.87-3.98 (m, 2H, CH=CH), 4.37 (m, 2H, NCH$_2$CH=CH), 6.24(t, 1H, NHCO), 6.90(t, 2H, PhCH2NH), 7.27-7.48 (m, 10H, ArH). IR (KBr): v3310, 3070, 2380, 1660, 1595, 1450, 1280, 1000, 980, 950, 745, 690.

Example 11

(IV-22) $N^1$-phenacyl-$N^4$-(2,4-difluorobenzylsulfonyl)piperazine hydrochloride A mixture of 2,4-difluorobenzylsulfonylchloride (3.5 mmol), N-phenacyl piperazine dihydrochloride (3 mmol), and $K_2CO_3$ (10.5 mmol) in 30 ml of DMF was treated according to the general preparation 2 to give compound (IV-22), 0.81 g (71%), $M^+$ 412.

Elemental analysis (found): $C_{19}H_{20}F_2N_2O_3S \cdot HCl \cdot 1.3/2H_2O$ (C, 57.21%; H, 5.89%; N, 7.10%). $^1$HNMR (DMSO-$d_6$): δ 3.56 (m, 8H, piperazine-H), 4.89(s, 2H, ClSO$_2$CH$_2$), 5.09(s, 2H, COCH$_2$N), 7.24-8.05(m, 8H, ArH).

Example 12

(IV-23) $N^1$-phenacyl-$N^4$-[2-(benzylamino)-2-oxoethyl] piperazine dihydrochloride This compound has the formula as defined in claim 1, wherein Ar$_1$ and Ar$_2$ represent phenyl respectively; R$_1$, R$_2$, and R$_3$, each represents hydrogen;

X represents amido; n=m$_1$=m$_2$=1.

A mixture of N-phenacyl piperazine dihydrochloride (1 g, 3.6 mmol), chloroacetyl-benzylamine (0.73 g, 4 mmol, prepared by chloroacetylchloride and benzylamine in 2N aqueous NaOH), KI (10 mg) and $K_2CO_3$ (1.8 g, 13 mmol) in 30 ml of DMF was stirred at 50° C. for 8 h, then filtered, and evaporated off the solvent, the residue was extracted with 20 ml of water and EtOAC (50 ml×3). Combined organic layer was washed with water and saline, dried (MgSO$_4$), filtered and evaporated. The residue was dissolved by 10 ml of ethanol and then adjusted to a PH of 2 by HCl/C$_2$H$_5$OH (5N), the resulting precipitate was recrystallized from aqueous ethanol or methanol to obtain compound (IV-23), 0.84 g (55%), mp208-210° C., $M^+$ 351.

Elemental analysis: $C_{21}H_{25}N_3O_2 \cdot 2HCl$. Found (wt %): C, 59.40; H, 6.45; N, 9.87. Theoretical (wt %): C, 59.55; H, 6.43; N, 9.93. IR (KBr): v 3180, 2950, 1690, 1670, 1570 cm$^{-1}$. $^1$HNMR(DMSO-$d_6$): δ 3.35-3.46 (m, 8H, piperazine-H), 3.89 (s, 2H, PhCH$_2$), 4.32 (s, 2H, NCH$_2$CON), 4.88 (s, 2H, COCH$_2$N), 7.23-7.96 (m, 10H, ArH), 9.13(s, NH).

Purity (HPLC): >99%

Example 13

(IV-26) $N^1$-(1-benzoylethyl)-$N^4$-[2-(benzylamino)-2-oxo-ethyl]piperazine dihydro-chloride A mixture of chloroacetylbenzylamine (3.06 mmol), N-[2-(benzylamino)-2-oxo-ethyl]piperazine dihydrochloride (3 mmol, prepared by using the general preparation 1) and $K_2CO_3$ (10.5 mmol) in 30 ml of DMF was treated according to the general preparation 2 to give compound (IV-26), 0.91 g (80%), $M^+$ 365.

Elemental analysis (found): $C_{22}H_{25}N_3 \cdot 2HCl \cdot H_2O$. $^1$HNMR(DMSO-$d_6$): δ1.74(d, J=6.0, 3H, COCH(CH$_3$)N), 3.56(m, 8H, piperazine-H), 4.14 (s, 2H, PhCH$_2$), 4.35(s, 2H, NCH$_2$CON), 5.44 (m, br, 1H, COCHN), 7.23-8.03 (m, 10H, ArH)

Example 14

(IV-28) $N^1$-(4-methoxyphenacyl)-$N^4$-[2-(benzylamino)-2-oxo-ethyl]piperazine dihydrochloride A mixture of chloroacetylbenzylamine (3.06 mmol), N-(4-methoxyphenacyl) piperazine dihydrochloride (3 mmol, prepared by using the general preparation 1) and $K_2CO_3$ (10.5 mmol) in 30 ml of DMF was treated according to the general preparation 2 to give compound (IV-28), 0.86 g (74%), $M^+$ 381.

Elemental analysis: $C_{22}H_{27}N_3O_3.2HCl.1/2H_2O$ $^1HNMR$ (DMSO-$d_6$): δ 3.56(m, 8H, piperazine-H), 3.77 (s, 3H, $CH_3O$), 4.14(s, 2H Ph$CH_2$), 4.35(s, 2H, N$CH_2$CON), 5.09 (s, 2H, CO$CH_2$N), 7.26-8.03 (m, 9H, ArH).

Example 15

(IV-29) $N^1$-phenacyl-$N^4$-[2-(R-1-phenylethanamino)-2-oxo-ethyl]piperazine dihydrochloride A mixture of (R)-2-chloro-N-(1-phenylethyl)acetamide (3 mmol), N-phenacyl piperazine dihydrochloride (2.5 mmol) and $K_2CO_3$ (8.75 mmol) in 30 ml of DMF was treated according to the general preparation 2 to give compound (IV-29), 0.72 g (63.2%), $M^+$ 365.

Elemental analysis: $C_{22}H_{27}N_3O_2.2HCl.H_2O$ $^1HNMR$ (DMSO-$d_6$): δ 1.44 (d, 3H, NHCH$CH_3$), 3.55 (m, 8H, piperazine-H), 4.04 (s, 1H, PhCH$CH_3$), 4.35(s, 2H, N$CH_2$CON), 5.12 (s, 2H, CO$CH_2$N), 7.23-8.14 (m, 10H, ArH).

Example 16

(IV-30) $N^1$-phenacyl-$N^4$-[2-(4-methoxybenzylamino)-2-oxo-ethyl]piperazine dihydrochloride A mixture of N-(4-methoxybenzyl)-2-chloroacetamide (3.65 mmol), N-phenacyl piperazine dihydrochloride (3.97 mmol) and $K_2CO_3$ (10.5 mmol) in 30 ml of DMF was treated according to the general preparation 2 to give compound (IV-30)(61%), $M^+$ 381.

Elemental analysis: $C_{22}H_{27}N_3O_3.2HCl.1/2H_2O$ $^1HNMR$ (DMSO-$d_6$):δ3.55(m, 8H, piperazine-H), 3.77(s, 3H, $CH_3O$), 4.14 (s, 2H Ph$CH_2$N), 4.35(s, 2H, N$CH_2$CON), 5.12 (s, 2H, CO$CH_2$N), 7.23-8.14 (m, 9H, ArH).

Example 17

(IV-31) $N^1$-phenacyl-$N^4$-[2-(2-pyridylmethylamino)-2-oxo-ethyl]piperazine trihydrochloride A mixture of 2-chloro-N-(pyridin-2-ylmethyl)acetamide (1.3 mmol), N-phenacyl piperazine dihydrochloride (1 mmol), and $K_2CO_3$ (8.75 mmol) in 30 ml of DMF was treated according to the general preparation 2 to give compound (IV-31), 0.7 g (60.45%), $M^+$ 381.

Elemental analysis: $C_{20}H_{24}N_4O_2.3HCl$ $^1HNMR$ (DMSO-$d_6$): δ3.33-3.54(m, 8H, piperazine-H), 4.33(s, 2H, NH$CH_2$), 4.39 (s, 2H, N$CH_2$CON), 5.12(s, 2H, CO$CH_2$N), 7.46-8.96 (m, 9H, ArH, pyridine-H).

Example 18

(IV-32) $^1$-phenacyl-$N^4$-[2-(3,4-methylenedioxyphenylmethylamino)-2-oxo-ethyl]piperazine dihydrochloride A mixture of N-[1-(3,4-methylenedioxyphenyl)methyl]-2-chloroacetamide (5 mmol), N-phenacyl piperazine dihydrochloride (5 mmol) and $K_2CO_3$ (17.5 mmol) in 60 ml of acetone was treated according to the general preparation 2 to give compound (IV-32), 0.76 g (63.45%), $M^+$ 395.

Elemental analysis: $C_{21}H_{25}N_2O_3.2HCl.1/2H_2O$ $^1HNMR$ (DMSO-$d_6$): δ2.42(s, 2H, O$CH_2$O), 3.33-3.54(m, 8H, piperazine-H), 4.33(s, 2H, NH $CH_2$), 4.39(s, 2H, N$CH_2$CON), 5.12 (s, 2H, CO$CH_2$N), 7.25-8.11 (m, 8H, ArH).

Example 19

(IV-33)$N^1$-[1-(5-chloro-6-methoxy-2-naphthoyl)ethyl]-$N^4$-[2-(benzylamino)-2-oxo-ethyl]piperazine dihydrochloride A mixture of chloroacetylbenzylamine (0.43 g, 2.3 mmol), N-[1-(5-chloro-6-methoxy-2-naphthoyl)ethyl]piperazine dihydrochloride (0.8 g, 1.9 mmol, prepared by using the general preparation 1) and $K_2CO_3$ (0.95 g, 6.6 mmol) in 40 ml of acetone was treated according to the general preparation 2 to give compound (IV-33), 0.86 g (60%), $M^+$ 480.

Elemental analysis (found): $C_{27}H_{30}ClN_3.2HCl.H_2O$ (C, 57.21%; H, 5.89%; N, 7.10%). $^1HNMR$(DMSO-$d_6$): δ1.68 (s, 3H, $CH_3$CH), 3.64-4.02(br, 11H, piperazine-H), 4.40(s, 3H, $OCH_3$), 5.37(t, 2H, PhCH2), 7.24-7.70(m, 10H, ArH), 8.34(m, 1H, NH).

Example 20

(IV-34) $N^1$-benzoyl-$N^4$-(2-phenylethyl-2-ol)piperazine hydrochloride

A mixture of N-benzyl-piperazine dihydrochloride (20 mmol, prepared by using the general preparation 3, yield 70%), 2-chloro-1-phenylethanone (24 mmol), $K_2CO_3$ (70 mmol) and KI(2 mmol) in 100 ml of acetone was treated according to the general preparation 2 to give $N^1$-benzyl-$N^4$-phenacyl piperazine dihydrochloride (67%).

The above product (3.5 mmol) in 60 ml of methanol was treated according to the general preparation 4 to give $N^1$-benzyl-N-$^4$-(phenylethyl-2-ol)piperazine dihydro-chloride (65%).

$N^1$-benzyl-$N^4$-(phenylethyl-2-ol)piperazine dihydrochloride (2.28 mmol) was treated according to the general preparation 5 to give N-(phenylethyl-2-ol)piperazine dihydrochloride (1.94 mmol) (85%), which was treated with benzoyl chloride (2.33 mmol) and $K_2CO_3$ (6.8 mmol) in 10 ml of DMF according to the general preparation 2 to give compound (IV-34), 0.51 g (76.4%), mp 116-118° C., $M^+$ 311.

Elemental analysis (found): $C_{19}H_{22}N_2O_2.HCl$ $^1HNMR$ (DMSO-$d_6$): δ3.27-3.65 (m, 10H, N$CH_2$, piperazine-H), 5.21 (m, 1H, CHOH), 7.27-7.47 (m, 10H, ArH). IR (KCl): v3300, 2940, 1625, 1490, 1100 $cm^{-1}$.

Example 21

(IV-36) $N^1$-phenacyl-$N^4$-(2-phenylethyl-2-ol) piperazine dihydrochloride

A mixture of N-(2-phenylethyl-2-ol) piperazine dihydrochloride (3 mmol, prepared in the similar procedure of example 20), 2-bromo-1-phenylethanone (3.6 mmol) and $K_2CO_3$ (10.5 mmol) in 15 ml of DMF was treated according to the general preparation 2 to give compound (IV-36), 0.81 g (67.2%), mp 220-221° C., $M^+$ 325.

Elemental analysis (found): $C_{20}H_{24}N_2O_2 \cdot 2HCl \cdot 1/2H_2O$. IR (KCl): v3300, 2970, 1690, 1620, 1590, 1060 $cm^{-1}$

Example 22

(IV-37) $N^1$-[2-(benzylamino)-2-oxo-ethyl]-$N^4$-(2-phenylethyl-2-ol) piperazine dihydrochloride A mixture of N-(2-phenylethyl-2-ol) piperazine dihydrochloride (2 mmol), N-benzyl-2-chloroacetamide (2.4 mmol), and $K_2CO_3$ (7 mmol) in 10 ml of DMF was treated according to the general preparation 2 to give compound (IV-37), 0.64 g (75.1%), mp 206-208° C., $M^+$ 354.

Elemental analysis (found): $C_{21}H_{27}N_3O_2 \cdot 2HCl$. IR (KCl): v 3350, 3220, 2980, 1680, 1600, 1540 $cm^{-1}$

Example 23

(IV-38) $N^1$-(4-methoxyphenacyl)-$N^4$-(3-phenylpropyl-3-ol) piperazine dihydrochloride A mixture of N-benzyl-piperazine dihydrochloride (2 mmol), 3-bromo-1-phenylpropan-1-one (36 mmol), $K_2CO_3$ (105 mmol) and KI (3 mmol) in 150 ml of acetone was treated according to the general preparation 2 to give $N^1$-benzyl-$N^4$-(3-oxo-3-phenylpropyl)-piperazine dihydrochloride (22 mmol)(73.2%).

A mixture of the above product (3.5 mmol) in 60 ml of methanol was treated according to the general preparation 4 to give $N^1$-benzyl-$N^4$-[(3-hydroxy-3-phenyl)propyl]piperazine dihydrochloride (2.6 mmol)(75%), which was treated according to the general preparation 5 to give N-[(3-hydroxy-3-phenyl)propyl]piperazine dihydrochloride (2.07 mmol)(83%).

The above product (2 mmol) was treated with 2-chloro-1-(4-methoxyphenyl)ethanone (2.4 mmol) and $K_2CO_3$ (7 mmol) in 10 ml of DMF according to the general preparation 2 to give compound (IV-38), 0.62 g (70.4%), mp 240-243° C., $M^+$ 368.

Elemental analysis (found): $C_{22}H_{28}N_2O_3 \cdot 2HCl$ (C, 60.21%; H, 7.03%; N, 6.31%).

Example 24

(IV-39) $N^1$-(4-chlorophenacyl)-$N^4$-(2-phenylethyl-2-ol)piperazine dihydrochloride A mixture of N-(2-phenylethyl-2-ol)piperazine dihydrochloride (2 mmol), 2-bromo-1-(4-chlorophenyl)ethanone (2.4 mmol) and $K_2CO_3$ (7 mmol) in 10 ml of DMF was treated according to the general preparation 2 to give compound (IV-39), 0.63 g (70%), $M^+$ 359.

Elemental analysis (found): $C_{20}H_{23}ClN_2O_2 \cdot 2HCl \cdot H_2O$. IR (KCl): v3300, 2960, 1700, 1620, 1570, 1060 $cm^{-1}$

Example 25

(IV-40) $N^1$-(4-methoxyphenacyl)-$N^4$-(2-phenylethyl-2-ol)piperazine dihydrochloride A mixture of N-(2-phenylethyl-2-ol)piperazine dihydrochloride (2 mmol), 2-bromo-1-(4-methoxyphenyl)ethanone (2.4 mmol) and $K_2CO_3$ (7 mmol) in 10 ml of DMF was treated according to the general preparation 2 to give compound (IV-40), 0.66 g (71%), $M^+$ 354.

Elemental analysis (found): $C_{21}H_{26}N_2O_3 \cdot 2HCl \cdot 2H_2O$. IR (KCl): v3300, 2950, 1690, 1625, 1550, 1060 $cm^{-1}$

Example 26

(IV-41) $N^1$-(1-benzoylethyl)-$N^4$-(2-phenylethyl-2-ol) piperazine dihydrochloride A mixture of N-(2-phenylethyl-2-ol) piperazine dihydrochloride (2 mmol), 2-bromo-1-phenylethanone (2.4 mmol) and $K_2CO_3$ (7 mmol) in 10 ml of DMF was treated according to the general preparation 2 to give compound (IV-41), 0.52 g (63%), $M^+$ 338.

Elemental analysis (found): $C_{21}H_{26}N_2O_2 \cdot 2HCl$ IR (KCl): v3300, 2870, 1750, 1610, 1590, 1030 $cm^{-1}$

Example 27

Preparation of Tablets

| | |
|---|---|
| The compound in this invitation | 15 mg |
| Starch | 55 mg |
| Sugar | 190 mg |
| Calcium stearate | 4 mg |

Example 28

Preparation of an Injection Fluid

| | |
|---|---|
| The compound in this invitation | 3 mg |
| Sodium chloride | 10 mg |
| Water | 50 mg |

Example 29

The Effect of the Compounds for the Maximum Contraction of the Ileo Muscles of Cavy Induced by L-Glu According to the literature (Luzzi, Br J Pharmacol, 95:1271, 1988), maximum contraction of isolated longitudinal ileomuscle preparations of guinea pig induced by L-Glu, were used to examine the activities of the compounds on the NMDA receptor.

Methods: L-Glu was used to induce the contraction of the isolated muscle preparations, Ketamine (the antagonist of NMDA receptor ion channel) and Ifenprodil (the antagonist of NMDA receptor polyamine site) were used as the positive control. 13 compounds were tested, the results indicate that 8 compounds could inhibit from the maximum contraction induced by Glu, showed the antagonistic activities on NMDA receptor ($10^{-5}$M); 5 compounds (IV-1, 9, 10, 11, 35) could excite preparations directly and induce preparations contraction, showed Glu-like excited action. The results were showed on Table 2.

TABLE 2

Activities of the Compounds on Inhibiting Muscle Contraction

| Compound | antagonism %* | Compound | excitation |
|---|---|---|---|
| IV-2 | 25 | IV-1 | $3 \times 10^{-6}$ |
| IV-3 | 37 | IV-9 | $10^{-5}$ |
| IV-5 | 30 | IV-10 | $10^{-5}$ |
| IV-6 | 25 | IV-11 | $10^{-5}$ |
| IV-7 | 25 | IV-35 | $3 \times 10^{-5}$ |
| IV-8 | 25 | L-Glu | $3.89 \times 10^{-5}$ |
| IV-23 | 40 | | |
| IV-34 | 25 | | |
| Ket | $5.61 \times 10^{-7}$ | | |
| Ifenprodil | 41%($10^{-5}$) | | |

*represents the restrain rate of compound ($10^{-5}$M) inducing the contraction of preparations Example 30

Anti-Cerebral Anoxia of the Compounds in Mice

With the mice models of anoxia induced by sodium nitrite (225 mg/kg, ip), the rate of the prolonging the survival duration of the mice was observed to evaluate the compound's activities of against anoxia. Of the 40 compounds (20 mg/kg sc) in this invention screened, the result showed that these compounds could prolong to various degrees the survival duration of the mice. The rates of the prolongation of 9 compounds (IV-2, 10, 23, 32, 34, 36, 39, 40, 41) were more than 50%, which indicated the effect of anti-cerebral anoxia. IV-23 and IV-2 prolonged the survival duration by 100% of the animals, showing remarkably protective action for cerebral anoxia. (Table 3)

Example 31

Protective Activities of the Compounds on Global Cerebral Ischemia in Rats

The animal models of the bilateral common carotid artery occlusion with exsanguine hypotension in the rats were used to investigate the effect against global cerebral ischemia.

Methods: The animals were administrated four compounds (IV-2, 23, 34, 36) orally for 3 days before the experiment. One hour after administration (20 mg/kg, 5 ml/kg), (saline (5 ml/kg) as vehicle group and Nimodipine (1 mg/kg) as positive control), the EEG recovery time of the rats on reperfusion after 10 min occlusion was observed to evaluate the effect of compounds on anti-cerebral ischemia. The results of the 4 compounds were shown on Table 4.

TABLE 4

Effects of the Compounds on Global Cerebral Ischemia in Rats

| Compound | n | Recovery time of EEG (min) |
|---|---|---|
| Saline | 6 | 22.00 ± 0.89 |
| Nimodipine | 6 | 13.49 ± 5.55 |
| IV-2 | 6 | 16.90 ± 0.86 |
| IV-23 | 9 | 13.32 ± 5.10 |
| IV-34 | 6 | 14.21 ± 2.33 |
| IV-36 | 6 | 20.10 |

The results indicate that compared with the saline group, 3 compounds (IV-23, IV-34 and IV-2) significantly shortened the recovery time of EEG after cerebral ischemia in rats. These results suggested that the compounds could protect brain from damage induced by ischemia-reperfusion. The activities of IV-23 and IV-34 were comparable with Nimodipine.

TABLE 3

Anti-cerebral Anoxia Activities of the Compounds

| Compound | Prolonging the survival duration (%) | Compound | Prolonging survival duration (%) | Compound | Prolonging survival duration (%) | Compound | Prolonging survival duration (%) |
|---|---|---|---|---|---|---|---|
| IV-1 | 3 | IV-2 | 100 | IV-3 | 7 | IV-5 | 22 |
| IV-6 | 4 | IV-7 | 21 | IV-8 | 21 | IV-9 | 30 |
| IV-10 | 60 | IV-11 | 2 | IV-13 | 32 | IV-16 | 30 |
| IV-17 | 14 | IV-18 | 25 | IV-19 | 18 | IV-21 | 33 |
| IV-22 | 26 | IV-23 | 100 | IV-24 | 34 | IV-25 | 30 |
| IV-26 | 36 | IV-32 | 58 | IV-34 | 60 | IV-35 | 42 |
| IV-36 | 65 | IV-37 | 13 | IV-39 | 85 | IV-40 | 60 |
| IV-41 | 55 | IV-44 | 3 | IV-48 | 16 | IV-49 | 30 |
| IV-53 | 15 | IV-54 | 25 | IV-55 | 4 | IV-56 | 25 |
| IV-58 | 25 | IV-61 | 22 | IV-62 | 36 | IV-64 | 20 |

Example 32

Effects of the Compounds on Focal Cerebral Ischemia in Rats

The focal ischemia rat model by occlusion of middle cerebral artery (MCA) was used to determine the protective effects of the compounds on focal cerebral ischemia. The infarct size after focal cerebral ischemia and the weight percentage of cerebral hemisphere were calculated to evaluate the compounds' effects on focal cerebral ischemia. The results of the two compounds (IV-20, 21, 22, 23, 33) are shown on Table 5.

TABLE 5

Effects of the Compounds (20 mg/kg p.o.) on Focal Cerebral Ischemia

|  | n | Neurological deficit After operation | Neurological deficit 24 h | Right hemisphere-Weight (g) | Infarct volume (g) | Percentage of infarct volume (%) |
|---|---|---|---|---|---|---|
| Saline | 10 | 9.6 ± 0.5 | 8.2 ± 1.8 | 0.74 ± 0.02 | 0.21 ± 0.08 | 28.8 ± 10.6 |
| Nimodipine | 8 | 9.3 ± 1.7 | 9.0 ± 4.1* | 0.730 ± 0.017* | 0.188 ± 0.013 | 25.7 ± 1.7 |
| IV-20 | 8 | 9.5 ± 0.6 | 8.8 ± 1.3* | 0.74 ± 0.01 | 0.14 ± 0.04 | 18.80 ± 5.61* |
| IV-21 | 8 | 9.8 ± 0.5 | 6.8 ± 2.5* | 0.76 ± 0.02 | 0.12 ± 0.07 | 15.53 ± 8.27* |
| IV-22 | 8 | 9.6 ± 0.9 | 7.4 ± 2.4* | 0.73 ± 0.01 | 0.10 ± 0.02 | 13.61 ± 3.31** |
| IV-23 | 8 | 9.4 ± 1.5 | 4.2 ± 1.3** | 0.737 ± 0.029 | 0.057 ± 0.012 | 13.3 ± 1.7** |
| IV-33 | 8 | 9.6 ± 0.6 | 8.4 ± 1.5* | 0.75 ± 0.02 | 0.12 ± 0.04 | 15.74 ± 5.70** |

*$P > 0.05$,
**$P < 0.01$ compared with saline group

Percentage of infarct volume: IV-23, IV-33 and IV-22 (20 mg/kg, ig) decreased the infarct region weight and percentage of infarct region weight to right hemisphere weight significantly ($p<0.01$); The Nimodipine group (20 mg/kg) showed no difference compared with the saline group ($p=0.072$).

Neurological deficit score: IV-23 decreased the rat Neurological deficit scores significantly, stronger than Nimodipine, 24 hours after operation. The results showed that compound IV-23 has a better protective effect on focal cerebral ischemia induced by occluded middle cerebral artery than others.

Example 33

Pharmacological Study of Compound IV-23

1. The Preclinical Pharmacodynamic Results of IV-23 in Animals
  (1) The Anti-Anoxia Effects of IV-23 in Mice
  a. Anoxia Caused by Sodium Nitrite One model was established to test the time needed for mice to die because of anoxia caused by sodium nitrite (225 mg/kg, ip). IV-23 (20 mg/kg, sc) can prolong the time for 100%, indicating significant anti-cerebral anoxic anoxia activity.

b. Anoxic Anoxia Experiment

Methods: Male Kunming mice were divided into 8 groups, 12 mice for each group. One group is injected subcutaneously with saline (0.2 mg/10 g, sc), other groups with ACEA1021 (NMDA receptor antagonist under clinical trial) or IV-23. 30 minutes after administration, the animals were put separately into wide-mouth bottles with soda lime, which more quickly closed. The survival time for each mice was recorded, and the group average of survival time was calculated and compared with the saline group.

Experimental results: The average survival time of the saline group was 14.05±0.65 minutes; The survival time of the IV-23 and ACEA-1021 groups was significantly longer in comparison (Table 6). $ED_{50}$ for IV-23 and ACEA-1021 were 6.2 mg/kg and 29.2 mg/kg, respectively, suggesting a protective effect of IV-23 for cerebral anoxia.

TABLE 6

Protective Effects of IV-23 on Mice Cerebral Anoxia

| Group | Dose (mg/kg, sc.) | Average survival time (min)(means ± S.E.M.) |
|---|---|---|
| Saline |  | 14.05 ± 0.65 |
| ACEA-1021 | 2.5 | 17.33 ± 1.18* |
|  | 5 | 18.20 ± 0.82** |
|  | 10 | 19.47 ± 1.17** |
|  | 20 | 20.04 ± 1.38** |
| IV-23 | 10 | 16.46 ± 0.89* |
|  | 20 | 17.11 ± 0.53** |
|  | 40 | 19.26 ± 0.91** |
|  | 80 | 20.04 ± 1.56** |

Note:
Compared with saline: *$p < 0.05$, **$p < 0.01$ (2) Protection of IV-23 Against Global Cerebral Ischemia in Rats The effect of IV-23 on cerebral ischemia-reperfusion in rats was studied using four arteries reversible occlusion by measuring the recovering time of the electroencephalogram and the righting reflex (a short time indicates a strong effect). IV-23 (5 mg/kg, 10 mg/kg, 20 mg/kg, ip, respectively) shortened obviously the recovering time and the righting reflex time compared with the saline group and the Nimodipine group (1 mg/kg, $p<0.01$), indicating that IV-23 has protection on global cerebral ischemia-reperfusion injury in rats.

TABLE 7

The Influence of IV-23 on Global Cerebral Ischemia-reperfusion Injury in Rats

| Group | N | Time for electroencephalogram to disappear(S) | Time for electroencephalogram to recover (S) | Time for righting reflex to recover (S) |
|---|---|---|---|---|
| Saline | 7 | 345.0 ± 380.5 | 2737.5 ± 1032.2 | 1895.0 ± 986.7 |
| Nimodipine | 5 | 396.0 ± 559.8$^\Delta$ | 3264.0 ± 336.4$^\Delta$ | 1284.0 ± 1319.8$^\Delta$ |
| High-dose | 4 | 566.3 ± 430.3$^{*\Delta}$ | 70.3 ± 20.1$^{***\Delta\Delta\Delta}$ | 147.0 ± 123.1$^{*\Delta\Delta\Delta}$ |
| Middle-dose | 7 | 557.1 ± 639.4$^{*\Delta}$ | 334.3 ± 674.3$^{***\Delta\Delta\Delta}$ | 822.8 ± 741.9$^{*\Delta\Delta}$ |
| Low-dose | 6 | 275.5 ± 338.1$^{*\Delta}$ | 184.6 ± 214.1$^{***\Delta\Delta\Delta}$ | 550.0 ± 282.5$^{*\Delta\Delta\Delta}$ |

$\Delta$ P > 0.05, $\Delta\Delta$ P < 0.05, $\Delta\Delta\Delta$ P < 0.01 compared with a saline group

*P > 0.05, P < 0.05, *P < 0.01 compared with a Nimodipine group (3) Protection of IV-23 on Focal Cerebral Ischemia in Rats.

a. The Focal Cerebral-Infarction of Using Electrical Coagulation to Occlude MCA:

The percentage for necrosis: compared with the vehicle control group, 10 mg/kg and 20 mg/kg of IV-23 significantly decreased the infarct size and the ratio between infarct size and the right cerebral hemisphere (p<0.01). For the 5 mg/kg group, the percentage of the rat's infarct size was decreased, but the difference is not significant (p=0.098). The effect is not significant for the Nimodipine mg/kg. The behavioral score of 24 hours after the operation: the score of the middle-dose and the high-dose groups were significantly decreased, the difference for middle-dose group was significantly (p<0.01) better than the group of Nimodipine. The results show that IV-23 has a great theraputic effect on the focal cerebral-infarction caused by ligation of MCA (Table 8), the effect is dose-related.

TABLE 8

The Effects of IV-23 on Rat Histology and Behavior Caused by Ligation of Cerebral Medium-Sized Artery

| Group | Number of the animal | The neurological deficit score After the operation | The neurological deficit score 24 h | The weight of the right cerebral hemisphere (g) | The weight of infarct area (g) | The percentage of infarction (%) |
|---|---|---|---|---|---|---|
| Negative criteria | 10 | 9.6 ± 0.5 | 8.2 ± 1.8 | 0.74 ± 0.02 | 0.21 ± 0.08 | 28.8 ± 10.6 |
| Nimodipine | 9 | 9.7 ± 0.5 | 8.3 ± 2.0* | 0.74 ± 0.01 | 0.15 ± 0.05 | 20.5 ± 6.8* |
| High-dose | 9 | 9.7 ± 0.5 | 6.7 ± 2.6* | 0.73 ± 0.02 | 0.11 ± 0.05 | 14.2 ± 6.8*** |
| middle-dose | 10 | 9.6 ± 0.5 | 5.6 ± 2.7** | 0.73 ± 0.01 | 0.10 ± 0.06 | 13.4 ± 8.4*** |
| Low-dose | 10 | 9.7 ± 0.5 | 8.1 ± 2.0* | 0.73 ± 0.01 | 0.15 ± 0.06 | 20.8 ± 8.8* |

*P > 0.05,

**P < 0.05,

***P < 0.01 compared with negative criteria a. Focal brain injury caused by photochemical induction of occlusion of the artery:

Compared with the vehicle (saline), IV-23 can significantly improve the rat's neurological deficit (p<0.05), decrease the weight of infarct area, the percent by weight of infarct area, per the right cerebra hemisphere (p<0.01). The percentage of infarction was lowered by 52% at 24 hours after operation. Compared with ACEA-1021, IV-23 can significantly reduce the neurological deficit score and the percentage of infarct area (p<0.01) (See Table 9).

The three models of focal cerebral ischemia showed that IV-23 reduces the volume of cerebral ischemic significantly, it has clear protective and therapeutic effects, and the effect is much better than that of Nimodipine and ACEA-1021.

TABLE 9

The Effect Of IV-23 on the Histology and Neurological Deficit Due to Occlusion of MCA Induced by Photochemical Reaction

| Group | Dose (mg/kg) | Number | Score of praxiology After operation | 24 h | Weight of right hemisphere (g) | Weight of necrotic area (g) | Necrotic percent (%) |
|---|---|---|---|---|---|---|---|
| Negative | 0 | 8 | 9.4 ± 0.5 | 9.1 ± 0.8 | 0.68 ± 0.01 | 0.16 ± 0.01 | 23 ± 1 |
| Positive | 2 | 8 | 9.5 ± 0.5 | 7.1 ± 1.9** | 0.70 ± 0.01 | 0.12 ± 0.02*** | 17 ± 2*** |
| IV-23 | 2 | 7 | 9.6 ± 0.5 | 5.4 ± 1.9***$^\Delta$ | 0.68 ± 0.01 | 0.08 ± 0.02***$^{\Delta\Delta\Delta}$ | 11 ± 3***$^{\Delta\Delta\Delta}$ |

*P > 0.05,
**P < 0.05,
***P < 0.01 compared with vehicle.
$^\Delta$P > 0.05,
$^{\Delta\Delta}$P < 0.05,
$^{\Delta\Delta\Delta}$P < 0.01 compared with positive control.

b. Temporary occlusion of the right MCA in rats caused by suture. The results show that ACEA-1021 can significantly reduce the ratio of volume after being under ischemia for 6 hours. Different doses of IV-23 can reduce the percent of volume of infarction significantly, and it is related with time of ischemia (Table 10). After 6 hours of ischemia, 5 mg/kg will significantly reduce the volume of the cerebral infarction; after 3 hours of ischemia, 5 mg/kg can reduce the volume by 46.3% (Table 11).

TABLE 10

Effects on Cerebral Ischemia (N = 10)

| Group | Dose (mg/kg) | Time of occlusine (hr) | Percent of infarct (%) (Means ± SEM) | P Value |
|---|---|---|---|---|
| Saline | | 1 | 3.76 ± 1.13 | |
| Saline | | 3 | 15.87 ± 2.28 | |
| Saline | | 6 | 20.00 ± 0.82 | |
| IV-23 | 5 | 1 | 1.31 ± 0.50 | $^a$>0.05 |
| IV-23 | 5 | 3 | 8.57 ± 1.42 | $^b$<0.05 |
| IV-23 | 5 | 6 | 12.90 ± 1.11 | $^c$<0.001 |

$^a$compared with saline for 1 hr
$^b$compared with saline for 3 hr
$^c$compared with saline for 6 hr

TABLE 11

Effects of Different Doses of IV-23 on Cerebral Ischemia

| Group | Dose (mg/kg) | Length of ischemia (hr) | Percent of volume (Means ± SEM) | P值* |
|---|---|---|---|---|
| Saline | | 6 | 20.00 ± 0.82 | |
| IV-23 | 2.5 | 6 | 15.42 ± 1.71 | <0.05 |
| IV-23 | 5 | 6 | 12.90 ± 1.11 | <0.001 |
| IV-23 | 10 | 6 | 14.92 ± 1.40 | <0.01 |
| ACEA-1021 | 10 | 6 | 12.73 ± 1.24 | <0.001 |

Example 34

Mechanism of IV-23 Effects on Cerebral Ischemia

1. Effects on the Hippocampal Neuron of Newborn Rats:

Electro-physiological Analysis: When tested using the whole-cell patch clamp technique with rapidly isolated rat CA1 pyramidal neuron, IV-23 inhibited the electric current induced by NMDA (100 μm), and the inhibitive effect showed dose dependency. $IC_{50}$: 562.7±1.1 μm(n=4, Hill coefficient 1.17), demonstrating that IV-23 inhibits the depolarization of the neuronal cell induced by NMDA, confirming that IV-23 is an antagonist of the NMDA receptor (See FIG. 1).

Methods: The whole-cell patch-clamp technique. Separate the rat's hippocampi, slash the brain piece into 500 μm thick. Get the CA1 area of hippocampi, put it into artificial cerebral spinal fluid (ACSF) to incubate for more than 1 hour. Then the solution is oxygen saturated. After the incubation of the brain piece, put it into ACSF with protease XIII (1 mg/ml) for 5 minutes. Using trypsin inhibitor type II-S (3 mg/ml) to terminate the protease digestion, and then using test tube to break the brain piece to obtain free cells, let it stand for a while and then start the experiment.

The electro-physiological experiment used the technique of whole-cell patch-clamp. The amplifier in the experiment is Axon-200A patch-clamp amplifier, with the DigiData-1200A as a sampling port. The software used is AxoScope Version 1.0. The experiment uses as a standard the electric current generated by the whole-cell. The effect of various samples on the electric current was observed. $IC_{50}$ was determined by proportion of different concentrations to the electric current of NMDA.

Results: IV-23 inhibits the electric current induced by NMDA in a concentration dependant way. $IC_{50}$ is 562.7±1.1 μm(n=4), the Hill Coefficient is 1.17, indicating IV-23's inhibition to the depolarization of the neuronal cells.

2. IV-23 Reduces Injury to Neuronal Cells Caused By NMDA:

Primary culture of rat cerebral cortical neuronal cells were used. The results showed that IV-23 significantly reduced the increase of LDH specific activity caused by NMDA in the supernatant of primary culture of neuronal cell (Table 12), indicating that IV-23 has a protective effect on the injury (Table 13). This is further evidence that IV-23 is a new NMDA receptor antagonist, and has anti-cerebral ischemic injury functions as well.

TABLE 12

Effect of NMDA on Neurons (n = 12)

| | Concentration (mmol/L) | LDH activities (U/g protein) (mean ± SEM) |
|---|---|---|
| Normal | | 0.68 ± 0.05 |
| | 0.1 | 1.51 ± 0.25** |
| | 0.5 | 1.63 ± 0.19** |
| NMDA | 1 | 1.74 ± 0.17** |
| | 2 | 2.38 ± 0.31** |

**P < 0.01, compared with normal

TABLE 13

Protective Effect of IV-23 on Neurons Damaged With NMDA (1 mmol/L) (N = 12)

| Concentration (mol/L) | LDH activities (U/g protein) | (mean ± SEM) | Protective rate (%) |
|---|---|---|---|
| Normal saline | | 1.74 ± 0.17 | |
| IV-23 | 10 | 1.86 ± 0.20 | 0 |
| | 50 | 1.23 ± 0.14* | 48.1 |
| | 100 | 1.05 ± 0.16** | 65.1 |
| | 200 | 0.79 ± 0.19** | 89.6 |

*P < 0.05, **P < 0.01, compared with normal saline group.

Example 35

3. Acute Toxicity of IV-23

$LD_{50}$ (mice, mg/kg, 95% confidence limit) of i.v. and p.o. are 132.77(115.79-147.86) mg/kg and 855.73(737.87-970.70) mg/kg, respectively.

4. The Genotoxicity of IV-23

The Ames test of IV-23 was negative.

The rodent microkernel experiment of IV-23 was negative.

The chromosome aberration trial in mammalian cultural cell was negative.

5. The Antiplatelet Agglutination of IV-23

At a concentration of $1 \times 10^{-4}$M, IV-23 did inhibit rats platelet aggregation induced by ADP, which suggested that its anti-cerebral infarction activities are not by the way of anticoagulation.

6. Conclusions:

IV-23 is a novel antagonist of NMDA receptor. It has an obvious effect on protecting the rats' primary culture nerve cell from the damage induced by NMDA. For focal cerebral infarction induced by rats' cerebral arterial ligation, oral administration (10 mg/kg) and injection (2.5 mg/kg) have evident therapeutic effects. IV-23's therapeutic action is better than Nimodipine and positive control ACEC-1021. IV-23 has a protective action against the global cerebral ischemia reperfusion damage. The induced mutation experiment is negative. IV-23 has shown obvious activity and safety on the models of rats' global and focal cerebral ischemia, indicating that it has preventive and therapeutic applications for human cerebral infraction.

We claim:

1. A compound of Formula I:

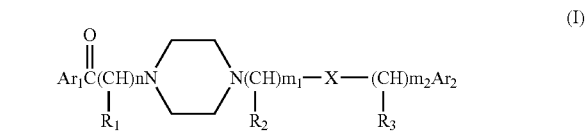

wherein $Ar_1$ and $Ar_2$ independently represent:

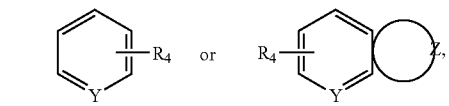

each of $R_1$, $R_2$, $R_3$ and $R_4$ represents hydrogen, a $C_1$-$C_3$ alkyl group, a $C_5$ or $C_6$ cycloalkyl group, phenyl, substituted phenyl, hydroxyl, methoxyl, ethoxyl, amino, substituted amino, halogen, carboxylic acid, carboxylic ester, nitryl, or acetonitrile group, X represents —CHOH—, —CO—, —CONH—, —CH═CH—, O, N, —SO$_2$— or —SO—, Y represents C, N, or O, Z represents a five or six-membered ring containing at least one of C, S, N or O, and n, $m_1$ and $m_2$ independent of one another represent 0, 1, 2, 3;

in the form of a racemate, enantiomer, diastereomer, a mixture of the enantiomers or diastereomers thereof, physiologically compatible acidic and basic salt, a salt with a cation or a base or with anions and/or acids or in the form of a free acid or base.

2. The compound of claim 1, wherein the salt is selected from the group consisting of hydrochloride, hydrobromide, sulfate, trifluoroacetate and methansulfonate.

3. The compound according to claim 2, wherein the salt is hydrochloride or hydrobromide.

4. The compound according to claim 1, wherein the salt contains about 0.5-3 molecules of hydrate water.

5. The compound according to claim 1, wherein each of $R_1$, $R_2$ and $R_3$ represents any one of hydrogen, a $C_1$-$C_3$ alkyl, hydroxyl, amino, substituted amino or carboxylic ester group; $R_4$ represents hydrogen, hydroxyl, alkoxy, nitryl, halogen, amino, substituted amino or a $C_1$-$C_3$ alkyl group.

6. The compound according to claim 1, wherein X represents —CHOH—, —CO— or —CONH—.

7. The compound according to claim 1, wherein Y represents C or N.

8. The compound according to claim 1, wherein the compound is selected from the group consisting of:

| IV-1 | $N^1$-benzoyl-$N^4$-phenacyl-piperazine, |
|---|---|
| IV-2 | $N^1,N^4$-diphenacyl-piperazine, |
| IV-3 | $N^1$-(4-nitrobenzoyl)-$N^4$-phenacyl-piperazine, |
| IV-4 | $N^1$-(2-acetoxy-1-oxo-2-phenylethyl)-$N^4$-(1-benzoylethyl) piperazine, |
| IV-5 | $N^1$-phenacyl-$N^4$-(4-chlorophenacyl) piperazine, |
| IV-6 | $N^1,N^4$-di (4-chlorophenacyl) piperazine, |

-continued

| | |
|---|---|
| IV-7 | $N^1$-(2-naphthoylmethyl)-$N^4$-phenacyl-piperazine, |
| IV-8 | $N^1$-(1-benzoylethyl)-$N^4$-phenacyl-piperazine, |
| IV-9 | $N^1$-phenacyl-$N^4$-(4-methoxyphenacyl) piperazine, |
| IV-10 | $N^1,N^4$-di (1-benzoylethyl) piperazine, |
| IV-11 | $N^1$-phenacyl-$N^4$-(4-nitrophenacyl) piperazine, |
| IV-12 | $N^1$-phenylacetyl-$N^4$-phenacyl-piperazine, |
| IV-13 | $N^1$-(1-benzoylethyl)-$N^4$-phenacyl-piperazine, |
| IV-14 | $N^1,N^4$-di (4-methoxyphenacyl) piperazine, |
| IV-15 | $N^1$-phenacyl-$N^4$-[(2-hydroxy) phenylacetyl] piperazine, |
| IV-16 | $N^1$-(4-methoxyphenacyl)-$N^4$-[(2-hydroxy) phenylacetyl] piperazine, |
| IV-17 | $N^1$-(1-benzoylethyl)-$N^4$-[2-hydroxy-2-(4-chlorophenyl)acetyl] piperazine, |
| IV-18 | $N^1$-(1-benzoylethyl)-$N^4$-[(2-hydroxy) phenylacetyl] piperazine, |
| IV-19 | $N^1$-phenacyl-$N^4$-[2-hydroxy-2-(4-chlorophenyl) acetyl] piperazine, |
| IV-20 | $N^1$-phenacyl-$N^4$-[1-(5-chloro-6-methoxy-2-naphthoyl) ethyl]piperazine, |
| IV-21 | N1-[2-(benzylamino)-2-oxo-ethyl]-$N^4$-cinnamyl piperazine, |
| IV-22 | $N^1$-phenacyl-$N^4$-(2,4-difluorobenzylsulfonyl) piperazine, |
| IV-23 | $N^1$-phenacyl-$N^4$-[2-(benzylamino)-2-oxo-ethyl] piperazine, |
| IV-24 | $N^1$-phenacyl-$N^4$-[2-(phenylamino)-2-oxo-ethyl] piperazine, |
| IV-25 | $N^1,N^4$-di[2-(benzylamino)-2-oxo-ethyl] piperazine, |
| IV-26 | $N^1$-(1-benzoylethyl)-$N^4$-[2-(benzylamino)-2-oxo-ethyl] piperazine, |
| IV-27 | $N^1$-(4-chlorophenacyl)-$N^4$-[2-(benzylamino)-2-oxo-ethyl] piperazine, |
| IV-28 | $N^1$-(4-methoxyphenacyl)-$N^4$-[2-(benzylamino)-2-oxo-ethyl] piperazine, |
| IV-29 | $N^1$-phenacyl-$N^4$-[2-(R-1-phenylethanamino)-2-oxo-ethyl] piperazine, |
| IV-30 | $N^1$-phenacyl-$N^4$-[2-(4-methoxybenzylamino)-2-oxo-ethyl] piperazine, |
| IV-31 | $N^1$-phenacyl-$N^4$-[2-(2-pyridylmethylamino)-2-oxo-ethyl] piperazine, |
| IV-32 | $N^1$-phenacyl-$N^4$-[2-(3,4-methylenedioxybenzylamino)-2-oxo-ethyl] piperazine, |
| IV-33 | $N^1$-[1-(5-chloro-6-methoxy-2-naphthoyl)ethyl]-$N^4$-[2-(benzylamino)-2-oxo-ethyl] piperazine, |
| IV-34 | $N^1$-benzoyl-$N^4$-(2-phenylethyl-2-ol) piperazine, |
| IV-35 | $N^1$-(4-nitrobenzoyl)-$N^4$-(2-phenylethyl-2-ol) piperazine, |
| IV-36 | $N^1$-phenacyl-$N^4$-(2-phenylethyl-2-ol) piperazine, |
| IV-37 | $N^1$-[2-(benzylamino)-2-oxo-ethyl]-$N^4$-(2-phenylethyl-2-ol) piperazine, |
| IV-38 | $N^1$-(4-methoxyphenacyl)-$N^4$-(3-phenylpropyl-3-ol) piperazine, |
| IV-39 | $N^1$-(4-chlorophenacyl)-$N^4$-(2-phenylethyl-2-ol) piperazine, |
| IV-40 | $N^1$-(4-methoxyphenacyl)-$N^4$-(2-phenylethyl-2-ol) piperazine, |
| IV-41 | $N^1$-(1-benzoylethyl)-$N^4$-(2-phenylethyl-2-ol) piperazine, |
| IV-42 | $N^1$-[2-(4-acetamidophenyl)-2-oxo-ethyl]-$N^4$-(2-phenylethyl-2-ol) piperazine, |
| IV-43 | $N^1$-(2-hydroxy-1-oxo-2-phenylethyl)-$N^4$-(phenylpropane-2-yl-3-ol) piperazine, |
| IV-44 | $N^1$-(S-2-hydroxy-1-oxo-2-phenylethyl)-$N^4$-(1-benzoylethyl) piperazine, |
| IV-45 | $N^1$-phenacyl-$N^4$-(3-fluorophenylmethylsulfonyl) piperazine, |
| IV-46 | $N^1$-phenacyl-$N^4$-(3-bromophenylmethylsulfonyl) piperazine, |
| IV-47 | $N^1$-phenacyl-$N^4$-(3-iodophenylmethylsulfonyl) piperazine, |
| IV-48 | $N^1$-phenacyl-$N^4$-(3-cyanophenylmethylsulfonyl) piperazine, |
| IV-49 | $N^1$-[1-(5-chloro-6-methoxy-2-naphthoyl)ethyl]-$N^4$-[2-(1-phenylethanamino)-2-oxo-ethyl] piperazine, |
| IV-50 | $N^1$-phenacyl-$N^4$-(2-fluorobenzylsulfonyl) piperazine, |
| IV-51 | $N^1$-phenacyl-$N^4$-(2,5-difluorobenzylsufonyl) piperazine, |
| IV-52 | $N^1$-phenacyl-$N^4$-(2,5-dichlorobenzylsufonyl) piperazine, |
| IV-53 | $N^1$-phenacyl-$N^4$-(4-phenoxybenzylsulfonyl) piperazine, |
| IV-54 | $N^1$-phenacyl-$N^4$-[2-(benzenesulfonylmethyl)benzylsulfonyl] piperazine, |
| IV-55 | $N^1$-phenacyl-$N^4$-(4-trifluoromethylbenzylsulfonyl) piperazine, |
| IV-56 | $N^1$-phenacyl-$N^4$-(4-phenylbenzylsulfonyl) piperazine, |
| IV-57 | $N^1$-phenacyl-$N^4$-(3-methoxybenzylsulfonyl) piperazine, |
| IV-58 | $N^1$-phenacyl-$N^4$-[4-(2-cyanophenyl)benzylsulfonyl] piperazine, |
| IV-59 | $N^1$-[2-(benzylamino)-2-oxo-ethyl]-$N^4$-(2,4-difluorobenzylsulfonyl) piperazine, |
| IV-60 | $N^1$-[2-(benzylamino)-2-oxo-ethyl]-$N^4$-(2,5-difluorophenylmethylsulfonyl) piperazine, |
| IV-61 | $N^1$-[2-(benzylamino)-2-oxo-ethyl]-$N^4$-[4-(2-cyanophenyl)benzylsulfonyl] piperazine, |
| IV-62 | $N^1$-[2-(benzylamino)-2-oxo-ethyl]-$N^4$-[2-(benzenesulfonylmethyl)benzyl sulfonyl] piperazine, |
| IV-63 | $N^1$-[2-(benzylamino)-2-oxo-ethyl]-$N^4$-(3,4-dichlorobenzylsulfonyl) piperazine, |
| IV-64 | $N^1$-[2-(benzylamino)-2-oxo-ethyl]-$N^4$-(4-nitrobenzylsulfonyl) piperazine, |
| IV-65 | $N^1$-[1-(5-chloro-6-methoxy-2-naphthoyl)ethyl]-$N^4$-[2-(benzylamino)-2-oxo-ethyl] piperazine, |
| IV-66 | $N^1$-[1-(5-chloro-6-methoxy-2-naphthoyl)ethyl]-$N^4$-(4-methoxyphenacyl) piperazine, |
| IV-67 | $N^1$-[1-(5-chloro-6-methoxy-2-naphthoyl)ethyl]-$N^4$-(4-chlorophenacyl) piperazine, |
| IV-68 | $N^1$-[1-(5-chloro-6-methoxy-2-naphthoyl)ethyl]-$N^4$-(4-methylsulfonylphenacyl) piperazine, |
| IV-69 | $N^1$-[2-(benzylamino)-2-oxo-ethyl]-$N^4$-[1-(5-chloro-6-methoxyl-naphthalen-2-yl)-propane-2-yl-1-ol] piperazine, and |
| IV-70 | $N^1$-(4-chlorophenacyl)-$N^4$-[1-(5-chloro-6-methoxyl-naphthalen-2-yl)-propane-2-yl-1-ol] piperazine. |

9. The compound according to claim 8, wherein the compound is $N^1$-phenacyl-$N^4$-[2-(benzylamino)-2-oxo-ethyl]piperazine.

10. A pharmaceutical composition comprising a compound according to claim 8, and a pharmaceutically acceptable excipient.

11. The pharmaceutical composition according to claim 10, wherein the compound is $N^1$-phenacyl-$N^4$-[2-(benzylamino)-2-oxo-ethyl]piperazine, which is in the form of a racemate, enantiomer, diastereomer, a mixture of the enantiomers or diastereomers thereof, physiologically compatible acidic and basic salt, a salt with a cation or a base or with anions and/or acids or in the form of a free acid or base.

12. A method for treating ischemic cerebral apoplexy, the method comprising administering to a patient in need thereof a pharmaceutical composition of claim 10.

13. A process for preparing a compound according to claim 1, wherein the process follows the following synthetic route:

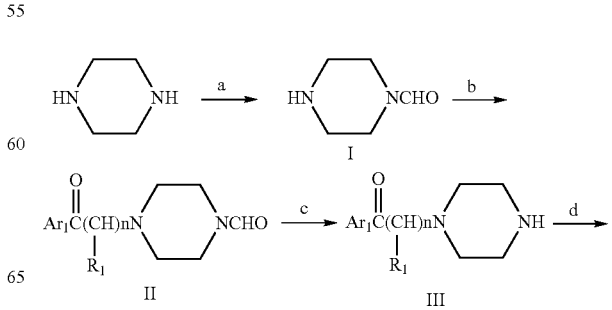

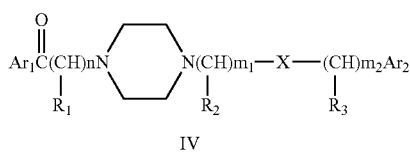

wherein:

X=—CHOH—, —CO—, —CONH or —SO$_2$—, and $m_1$, $m_2$, or n is 0, 1, 2, or 3; and wherein the reaction medium for steps a, b, c and d comprises the following components:

a: HCOOCH$_3$   b: Ar$_1$CO(CH)$_n$CL, K$_2$CO$_3$, KI, CH$_3$COCH$_3$,
              |
              R$_1$ c: NaOH   d: Ar$_2$(CH)m$_2$—X—(CH)m$_1$CL, K$_2$CO$_3$, KI, DMF.
              |              |
              R$_3$          R$_2$

14. A process for preparing a compound according to claim 1, wherein the process follows the following synthetic route:

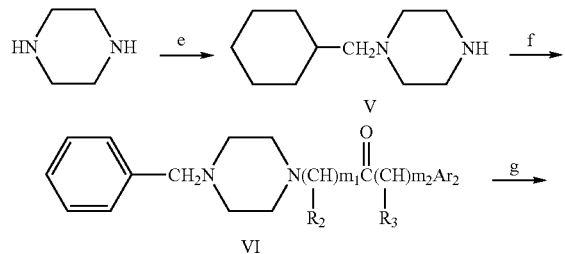

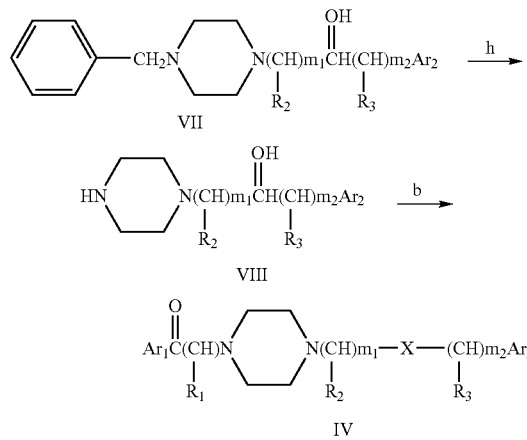

wherein X=CHOH wherein $m_1$, $m_2$, or n is 0, 1, or 3 and wherein the reaction medium for steps e, f, g, h and b comprises the following components:

b: Ar$_1$CO(CH)$_n$CL, K$_2$CO$_3$, KI, CH$_3$COCH$_3$,
       |
       R$_1$ e: PhCH$_2$Cl, KOH, CTBA, Ph/H$_2$O, f: Ar$_2$(CH)m$_2$—CO—(CH)m$_1$CL, K$_2$CO$_3$, KI, CH$_3$COCH$_3$,
       |              |
       R$_3$          R$_2$ g: KBH$_4$, CH$_3$OH h: 10% Pd—C/H$_2$, HAc.

* * * * *